United States Patent
Niebes et al.

(10) Patent No.: US 9,844,595 B2
(45) Date of Patent: *Dec. 19, 2017

(54) COMPOSITION COMPRISING A COMPLEX OF (+)-CATECHIN AND AMINO ACID FOR THE TREATMENT AND PREVENTION OF CANCER

(71) Applicant: VALORE, Seneffe (BE)

(72) Inventors: Paul Niebes, Grez-Doiceau (BE); Bronislav Henric May, Overijse (BE); Saïd Rachidi, Hyon (BE); Julien Estager, Kontich (BE); Bruno Schoentjes, Ville d'Avray (FR)

(73) Assignee: Valore, Seneffe (BE)

( * ) Notice: Subject to any disclaimer, the term of this patent is extended or adjusted under 35 U.S.C. 154(b) by 0 days.

This patent is subject to a terminal disclaimer.

(21) Appl. No.: 14/889,470

(22) PCT Filed: May 13, 2014

(86) PCT No.: PCT/EP2014/059780
§ 371 (c)(1),
(2) Date: Nov. 6, 2015

(87) PCT Pub. No.: WO2014/184197
PCT Pub. Date: Nov. 20, 2014

(65) Prior Publication Data
US 2016/0089358 A1    Mar. 31, 2016

(30) Foreign Application Priority Data

May 17, 2013    (BE) .................................. 2013/0350

(51) Int. Cl.
| *A61K 31/35* | (2006.01) |
| *A01N 43/16* | (2006.01) |
| *A61K 47/18* | (2017.01) |
| *A61K 31/19* | (2006.01) |
| *A61K 31/194* | (2006.01) |
| *A61K 31/198* | (2006.01) |
| *A61K 31/353* | (2006.01) |
| *A61K 31/375* | (2006.01) |
| *A61K 9/00* | (2006.01) |
| *A61K 9/08* | (2006.01) |

(52) U.S. Cl.
CPC .......... *A61K 47/183* (2013.01); *A61K 9/0053* (2013.01); *A61K 31/19* (2013.01); *A61K 31/194* (2013.01); *A61K 31/198* (2013.01); *A61K 31/353* (2013.01); *A61K 31/375* (2013.01); *A61K 9/0095* (2013.01); *A61K 9/08* (2013.01)

(58) Field of Classification Search
CPC .... A61K 31/19; A61K 31/194; A61K 31/198; A61K 31/353; A61K 31/375; A61K 47/183; A61K 9/0053; A61K 9/0095; A61K 9/08
USPC ........................................................ 514/456
See application file for complete search history.

(56) References Cited

U.S. PATENT DOCUMENTS

| 4,285,964 A | 8/1981 | Niebes et al. |
| 7,041,699 B2 * | 5/2006 | Netke ................... A23L 33/175 424/630 |
| 9,211,298 B2 * | 12/2015 | Gao ........................ A61K 31/05 |
| 2003/0130201 A1 | 7/2003 | Netke et al. |
| 2005/0032715 A1 | 2/2005 | Netke et al. |
| 2005/0281794 A1 | 12/2005 | Netke et al. |
| 2016/0095923 A1 * | 4/2016 | Niebes ................. A61K 47/183 514/456 |

FOREIGN PATENT DOCUMENTS

| CH | 665 634 A5 | 5/1988 |
| CN | 1 943 572 A | 4/2007 |
| GB | 2 306 321 A | 5/1997 |
| WO | WO 2007137602 A1 * | 12/2007 ........... A61K 9/0095 |

OTHER PUBLICATIONS

PCT International Preliminary Report on Patentability and Written Opinion of the International Searching Authority dated Nov. 17, 2015 for PCT International Patent Application No. PCT/EP2014/059780,12 pages with English Translation of the Written Opinion.
PCT International Search Report dated Sep. 17, 2014 for PCT International Patent Application No. PCT/EP2014/059780, 4 pages.
Weyant M J et al., entitled "(+)-Catechin Inhibits Intestinal Tumor Formation and Suppresses Focal Adhesion Kinase Activation in the Min/+Mouse," Cancer Research 61, 118-125, Jan. 1, 2001.

* cited by examiner

*Primary Examiner* — My-Chau T Tran
(74) *Attorney, Agent, or Firm* — Amster, Rothstein & Ebenstein LLP

(57) ABSTRACT

The invention relates to a gastroenteric therapeutic composition for oral administration, comprising a compound of monomeric (+)-catechin and at least one basic amino acid, said composition being characterized in that it is used in the form of a complex of (+)-catechin and at least one basic amino acid or at least one derivative or precursor of a basic amino acid for the curative and/or preventive treatment of cancer, said complex having a molar equivalence ratio of the monomeric (+)-catechin to the at least one basic amino acid or the at least one basic amino acid derivative of between 1:1 and 1:2.5.

20 Claims, 8 Drawing Sheets

COMPOSITION COMPRISING A COMPLEX OF (+)-CATECHIN AND AMINO ACID FOR THE TREATMENT AND PREVENTION OF CANCER

CROSS-REFERENCE TO RELATED APPLICATIONS

This application is a U.S. national stage entry under 35 U.S.C. §371 of PCT International Patent Application No. PCT/EP2014/059780, filed May 13, 2014, which claims priority to Belgian Patent Application No. 2013/0350, filed May 17, 2013, the contents of which are incorporated herein by reference in their entirety.

The present invention relates to a gastroenteric composition for oral administration, comprising a compound of monomeric (+)-catechin and at least one basic amino acid, intended for mammals, and in particular for human beings.

Polyphenols constitute a family of organic molecules widely present in the plant kingdom. They are characterized, as the name indicates, by the presence of several phenolic groups combined in structures generally of high molecular weight. These compounds are the products of secondary metabolism in plants.

In particular, (+)-catechin in its monomeric form is directly obtained from *Uncaria gambir* extract.

Such a composition is already known, for example, from document U.S. Pat. No. 4,285,964 in the context of the treatment of chronic diseases of degenerative type of connected tissues. Among these degenerative diseases, including the most well known and most widespread in human beings, are for example arthrosis, chondromalacia and parodontosis.

According to document U.S. Pat. No. 4,285,964, the composition comprising a compound of monomeric (+)-catechin and at least one basic amino acid is a medicament in which the active substance is the monomeric (+)-catechin.

Document U.S. Pat. No. 4,285,964 relates mainly to an injectable composition. However, this document extrapolates in passing the abovementioned injectable composition in order to obtain an oral formulation by drying the injectable composition.

The present invention relates to a novel use of the oral composition mentioned at the beginning for the curative and/or preventive treatment of cancer, preferably hepatocellular cancer, said monomeric (+)-catechin having a molar equivalence ratio relative to said at least one basic amino acid or to a basic amino acid derivative (or else an amino acid precursor) of between 1:1 and 1:2.5.

The use of monomeric (+)-catechin as a treatment of cancer in mammals is known from the article by Weynant M. J., Carothers A. M., Dannenberg A. J., and Betragnolli M. M., published in 2001 in *Cancer Research*, volume 61, page 118.

This article describes the treatment of intestinal tumors in mice using pure monomeric (+)-catechin administered orally, and therefore certainly not linked to one or more amino acids. In particular, this article stipulates that, by virtue of its high bioavailability when administered orally, monomeric (+)-catechin is a promising active agent for the treatment of a wide variety of tumors of epithelial type in mammals, preferably in human beings.

Unfortunately, while this article makes promising conclusions, the latter remain hypothetical insofar as it does not demonstrate the transposition of the results from mice to humans.

In the context of the present invention, it has been observed entirely surprisingly that the composition based on monomeric (+)-catechin and at least one basic amino acid or at least one derivative of a basic amino acid, when it is administered orally, allows treatment and prevention, preferably improved prevention, of cancer in mammals, and in particular in humans.

The anticancer action is explained by the still as yet unexplained properties of the composition according to the invention, which are the following:
- a membrane-stabilizing action;
- properties of protection of the web of the connected tissues which surround the organs of mammals; and
- a directly protected action on the gastric mucosa reputed to be subject to ulcers and to carcinoid tumors.

In addition, as is in fact demonstrated by the applicants, the presence of said at least one amino acid (or of said at least one amino acid derivative or precursor), in the equivalence ratio as claimed, makes it possible to exacerbate the anticancer action of the monomeric (+)-catechin in an unexpected manner.

Preferably, said molar equivalence ratio is between 1:1 and 1:2.

Advantageously, said molar equivalence ratio is a ratio of 1:1 or of 1:2.

Preferably, said molar equivalence ratio is greater than or equal to 1:1, in particular greater than 1:1.

Advantageously, said molar equivalence ratio is less than or equal to 1:2.5.

In particular, said molar equivalence ratio is less than 2.5, more particularly less than or equal to 1:2.

Preferentially, said molar equivalence ratio is less than 2.

Preferably, said molar equivalence ratio is greater than or equal to 1:1, in particular greater than 1:1.

Advantageously, said molar equivalence ratio is less than or equal to 1:2.5.

In particular, said molar equivalence ratio is less than 1:2.5, more particularly less than or equal to 1:2.

Preferentially, said molar equivalence ratio is less than 1:2.

Alternatively, the molar equivalence ratio is between 1:1.5 and 1:2.5, preferably between 1:1.5 and 1:2.

Advantageously, said molar equivalence ratio is greater than or equal to 1.00:1.00 and less than or equal to 1.00:2.50.

Very advantageously, said molar equivalence ratio is greater than or equal to 1.00:1.00 and less than or equal to 1.00:1.50.

Preferably, said molar equivalence ratio is greater than or equal to 1.00:1.50 and less than or equal to 1.00:2.00.

Preferably, said molar equivalence ratio is greater than or equal to 1.00:1.50 and less than or equal to 1.00:2.50.

Preferably, said composition is used in the form of a complex of (+)-catechin and of at least one basic amino acid or of at least one derivative of a basic amino acid, said complex having a molar equivalence ratio of said monomeric (+)-catechin relative to said at least one basic amino acid or to said at least one basic amino acid derivative of between 1:1 and 1:2.5 (hereinafter referred to as a [C:AA/ 1:1-1:2.5] complex).

Preferably, said molar equivalence ratio is between 1:1 and 1:2.

Advantageously, said molar equivalence ratio is a ratio of 1:1 or of 1:2.

Preferably, said molar equivalence ratio is greater than or equal to 1:1, in particular greater than 1:1.

Advantageously, said molar equivalence ratio is less than or equal to 1:2.5.

In particular, said molar equivalence ratio is less than 2.5, more particularly less than or equal to 1:2.

Preferentially, said molar equivalence ratio is less than 2.

Preferably, said molar equivalence ratio is greater than or equal to 1:1, in particular greater than 1:1.

Advantageously, said molar equivalence ratio is less than or equal to 1:2.5.

In particular, said molar equivalence ratio is less than 1:2.5, more particularly less than or equal to 1:2.

Preferentially, said molar equivalence ratio is less than 1:2.

Alternatively, the molar equivalence ratio is between 1:1.5 and 1:2.5, preferably between 1:1.5 and 1:2.

Advantageously, said molar equivalence ratio is greater than or equal to 1.00:1.00 and less than or equal to 1.00:2.50.

Very advantageously, said molar equivalence ratio is greater than or equal to 1.00:1.00 and less than or equal to 1.00:1.50.

Preferably, said molar equivalence ratio is greater than or equal to 1.00:1.50 and less than or equal to 1.00:2.00.

Preferably, said molar equivalence ratio is greater than or equal to 1.00:1.50 and less than or equal to 1.00:2.50.

Preferably, said at least one basic amino acid is lysine.

The use of the [C:AA/1:1-1:2.5] complex in the context of oral treatment and prevention against cancer is made possible by virtue of the high bioavailability, when administered orally, of the (+)-catechin when it is complexed with at least one basic amino acid or at least one derivative, or else a precursor, of a basic amino acid, this property having to date not yet been disclosed.

It is in fact thought that the presence of said at least one basic amino acid linked to the monomeric (+)-catechin allows the complex to easily cross the intestinal wall; this therefore results in a higher proportion of free monomeric (+)-catechin in the blood.

In their article, Weynant M. J. et al. do not define what they mean by high bioavailability, in particular when administered orally.

On the basis of the results presented in the context of the present invention, it is observed that the high bioavailability, when administered orally, of one gram of monomeric (+)-catechin in the form of a complex reaches a value of at least 900 ng h/ml (54 000 ng min/ml) in humans. In light of the results of the present invention, the term "high bioavailability in humans" is therefore intended to mean a bioavailability at least equal to 900 ng h/ml (54 000 ng min/ml) for an oral administration of one gram.

The results obtained by the inventors of the present patent application show that the bioavailability measured in humans for one gram of (+)-catechin ingested in the form of a complex of monomeric (+)-catechin and of at least one basic amino acid in a molar equivalence ratio of between 1:1 and 1:2.5 is at least 900 ng h/ml (54 000 ng min/ml).

By way of illustration, it is observed in the context of this invention that the bioavailability, when administered orally in human beings, of the (+)-catechin ingested in the form of a complex of monomeric (+)-catechin is much higher [1263±88 ng h/ml (75 780 ng min/ml) for 0.920 g of monomeric (+)-catechin ingested in the form of 1.5 g of complex] than that of the monomeric (+)-catechin ingested alone [832±150 ng h/ml (49 920 ng min/ml) for an equivalent amount of 0.920 g of an oral intake of pure monomeric (+)-catechin], i.e. +52% increase in bioavailability by virtue of the complex.

This characteristic is all the more unexpected since it has been demonstrated in the context of the present invention that the pure monomeric (+)-catechin has a solubility in water which is 400 times lower than that measured when it is solubilized in the form of a complex formed with at least one basic amino acid or at least one derivative of a basic amino acid.

Indeed, the solubility of the lysine salts of the (+)-catechin reaches, at 20° C., 400 g per liter of water, whereas the (+)-catechin itself exhibits, under the same conditions, a solubility of 0.9 g per liter.

Two other important advantages should be noted.

Firstly, the use of (+)-catechin administered orally in the form of a [C:AA/1:1-1:2.5] complex gives a maximum plasma concentration of free monomeric (+)-catechin, c (max), that is more than doubled compared with that obtained with the same dose of pure monomeric (+)-catechin ingested under the same conditions: c (max) of 571 ng for 1 g of (+)-catechin ingested in the form of a complex, compared with 280 ng for 1 g of monomeric (+)-catechin ingested as it is, i.e. an increase of +103%.

Secondly, these more than doubled maximum plasma concentrations are reached [T (max)] more than two times faster when the (+)-catechin is ingested in the form of a [C:AA/1:1-1:2.5] complex rather than in the form of monomeric (+)-catechin alone: T (max) of 30 min compared with 80 min, i.e. an increase of +166%.

All these characteristics constitute genuine advantages particularly in the case of a medicament intended for the prevention and/or treatment of cancer. Since the doses to be administered are in this case often very high and to be taken long-term, it is advantageous not only to be able to reduce them by virtue of the [C:AA] complex, but in addition to directly obtain, after taking this complex, blood levels that are more than doubled with respect to those that would be obtained with the molecule alone.

Since the (+)-catechin is generally well tolerated, the only complaint at high dose is indigestion, which could consequently be eliminated or at the very least reduced by using the [C:AA/1:1-1:2.5] complex in the context of the treatment of long duration.

In addition, it is demonstrated in the present invention that the oral use of the complex according to the invention for the treatment and prevention of cancer has been proven to be at least as effective as use of said composition by injection.

Indeed, it is a bioavailability for the [C:AA/1:1-1:2.5] complex, when administered orally, which is higher by a factor of 1.90 than that when administered by injection, in rats, that is demonstrated in the present invention.

It is also demonstrated that the (+)-catechin, once injected, is rapidly metabolized and eliminated from the body (in a period of one hour following the injection, close to 90% of the content of free monomeric (+)-catechin has been eliminated from the blood). In the case of an oral absorption, a peak concentration of free monomeric (+)-catechin in the blood is observed within a period of one hour after absorption, and a decrease of 50% of this content is observed after two hours.

This means that the oral assimilation makes it possible to maintain a proportion of free monomeric (+)-catechin in the blood which is delayed over time, and therefore an improved anticancer action.

Finally, since the results obtained in rats with regard to the treatment of cancer by taking the complex according to the invention per os agree well with those obtained in humans, the transposition of the results in rats to the situation in humans is therefore proven.

In rats having ingested 150 mg/kg of (+)-catechin hydrochlorolysinate, the bioavailability of free (+)-catechin in the blood is 132 349 ng min/ml (2206 ng h/ml), whereas in humans, the ingestion of 1.5 g of the same (+)-catechin hydrochlorolysinate gives a bioavailability of 75 780 ng min/ml (1263 ng h/ml). Considering the fact that the metabolism is accelerated in rats, it is found that, for the bioavailability studies subsequently mentioned, the results are transposable to humans (see tables 4 and 2).

The present application makes reference to the fact that the monomeric (+)-catechin represents an alternative to the more extensive treatments represented by rays or chemotherapy, in the context of the treatment of cancer, in particular hepatocellular cancer.

Preferably, said at least one basic amino acid is lysine.

In one preferential embodiment of the present invention, said complex is a complex comprising one molecule of lysine for one molecule of monomeric (+)-catechin.

In one advantageous embodiment of the present invention, said complex is a complex comprising one molecule of arginine for one molecule of monomeric (+)-catechin.

In one particular embodiment of the present invention, said complex is a complex comprising two molecules of lysine for one molecule of monomeric (+)-catechin.

The complex of (+)-catechin with two lysines is by far, in all the experiments, the best combination for improving the bioavailability of the monomeric (+)-catechin when administered orally.

In another particular embodiment of the present invention, said complex is a complex comprising two molecules of arginine for one molecule of monomeric (+)-catechin.

In another preferential form, said complex is a complex comprising one molecule of lysine and one molecule of arginine for one molecule of monomeric (+)-catechin.

Preferably, the composition according to the invention is characterized in that said complex is in the form of a salt of said complex, said salt comprising said complex, said complex comprising at least one proton derived from at least one acid and at least one anion derived from said at least one acid, said salt exhibiting said proton in equimolar amount relative to the amount of basic amino acid or of basic amino acid derivative.

In this way, the complex salt is defined by the following formulae:

[C:AA:H$^+$:A$^-$/1:x:x:x], in the case of a monofunctional acid such as HCl; or

[C:xAA:xH$^+$:x/yA$^{y-}$], in the case of an acid,

H$^+$ representing the proton of the acid,
A$^-$ representing the anion of the acid,
x representing the number of molar equivalents of AA,
y representing the charge carried by the anion.

Advantageously, said at least one acid is preferably chosen from ascorbic acid, acetic acid, citric acid and hydrochloric acid. Very advantageously, said acid is ascorbic acid.

The role of ascorbic acid is that of a vitamin supplement. Furthermore, since this acid is also an antioxidant, it therefore plays a synergistic antioxidant role with respect to that of the (+)-catechin.

This addition of an acid also makes it possible to improve the bioavailability of the (+)-catechin when administered orally. This observation is explained by the more stable state of the (+)-catechin in an acidic medium.

In one particular embodiment, said composition is characterized in that it also comprises one or more biocompatible excipients.

Preferably, the content of complex of (+)-catechin with said basic amino acid or said at least one derivative of a basic amino acid is between 15% and 95% by weight relative to the total weight of said composition, preferably between 60% and 90%, advantageously from 65% to 85%.

Preferably, the composition is in liquid form or in solid form, preferably water-soluble solid form, in particular in the form of a powder, a tablet or a lozenge.

Advantageously, the composition in liquid form has, in a 0.01 molar solution at 25° C., a pH greater than or equal to 3 (i.e. the theoretical pH of a [C:Lys:H$^+$:A$^-$] salt in a molar equivalence ratio of 1:0.5), preferably of between 4 and 11, advantageously between 4.5 and 9.

Optionally, the composition according to the invention is a solid composition, with a pH greater than or equal to 3, preferably of between 4 and 11, advantageously between 4.5 and 9, when it is dissolved at 0.01 M at 25° C., comprising monomeric (+)-catechin and said at least one basic amino acid or said at least one basic amino acid derivative, and optionally at least one acid, as precursors of said complex or of said salt of the complex, as a combined preparation for simultaneous oral use, said complex forming post-oral administration.

The solid composition according to the invention comprises the monomeric (+)-catechin and said at least one basic amino acid or said at least one basic amino acid derivative in a molar equivalence ratio of between 1:1 and 1:2.5.

Preferably, said molar equivalence ratio is greater than or equal to 1:1, in particular greater than 1:1.

Advantageously, said molar equivalence ratio is less than or equal to 1:2.5.

In particular, said molar equivalence ratio is less than 1:2.5, more particularly less than or equal to 1:2.

Preferentially, said molar equivalence ratio is less than 1:2.

Alternatively, the molar equivalence ratio is between 1:1.5 and 1:2.5, preferably between 1:1.5 and 1:2.

Advantageously, said molar equivalence ratio is greater than or equal to 1.00:1.00 and less than or equal to 1.00:2.50.

Very advantageously, said molar equivalence ratio is greater than or equal to 1.00:1.00 and less than or equal to 1.00:1.50.

Preferably, said molar equivalence ratio is greater than or equal to 1.00:1.50 and less than or equal to 1.00:2.00.

Preferably, said molar equivalence ratio is greater than or equal to 1.00:1.50 and less than or equal to 1.00:2.50.

The monomeric (+)-catechin and said at least one basic amino acid, or said at least one basic amino acid derivative, are precursors which participate, in an aqueous medium, in a complexation reaction so as to form the complex according to the invention.

In this case, the complex is formed in vivo in the gastrointestinal tract of contact with the water of the saliva or with the water contained in stomach bolus.

Alternatively, the composition according to the invention is a solid composition comprising monomeric (+)-catechin and said at least one basic amino acid or said at least one basic amino acid derivative, and optionally at least one acid, as precursors of said complex or of said salt of the complex, as a combined preparation for simultaneous oral use in solution in an aqueous phase, said complex forming pre-oral administration, said monomeric (+)-catechin and said at least one basic amino acid or said at least one basic amino acid derivative being present in a molar equivalence ratio of between 1:1 and 1:2.5.

Preferably, said molar equivalence ratio is greater than or equal to 1:1, in particular greater than 1:1.

Advantageously, said molar equivalence ratio is less than or equal to 1:2.5.

In particular, said molar equivalence ratio is less than 1:2.5, more particularly less than or equal to 1:2.

Preferentially, said molar equivalence ratio is less than 1:2.

Alternatively, the molar equivalence ratio is between 1:1.5 and 1:2.5, preferably between 1:1.5 and 1:2.

Advantageously, said molar equivalence ratio is greater than or equal to 1.00:1.00 and less than or equal to 1.00:2.50.

Very advantageously, said molar equivalence ratio is greater than or equal to 1.00:1.00 and less than or equal to 1.00:1.50.

Preferably, said molar equivalence ratio is greater than or equal to 1.00:1.50 and less than or equal to 1.00:2.00.

Preferably, said molar equivalence ratio is greater than or equal to 1.00:1.50 and less than or equal to 1.00:2.50.

In this way, the complex is formed as soon as the composition is placed in aqueous solution, i.e. before oral administration.

Preferably, said oral composition is characterized in that it is used in the prevention and treatment of a variety of forms of cancer, including chronic or non-chronic leukemias, liver cancer, prostate cancer, breast cancer, uterine cancer, testicular cancer, bladder cancer, kidney cancer, lung cancer, bronchial cancer, bone cancer, mouth cancer, esophageal cancer, stomach cancer, pancreatic cancer, colorectal cancer, lymphomas and myelomas, but not exclusively.

Indeed, it has been demonstrated in the context of the present invention that said oral or injectable (parenteral) composition prevents tumors from spreading, helps the body to recover after chirurgical ablation of cancers and reduces the toxic effect of other medicaments used in chemotherapy. It is also demonstrated here that said composition likewise reduces the destruction of connective tissue and in particular that of collagen fibers during radiotherapy.

Other embodiments of the composition based on the complex according to the invention are indicated in the appended claims.

The present invention also relates to the use of an oral therapeutic composition based on the complex or on the complex salt according to the invention, for the treatment and/or prevention of cancer.

The present invention also relates to the use of the composition according to the invention, for the production of an oral therapeutic composition for the treatment and prevention of cancer in mammals, and in particular in human beings.

Other characteristics and advantages of the invention will emerge from the description given hereinafter, in a nonlimiting manner and with reference to the examples (and in particular to the comparative examples) described below.

Figure 1A:
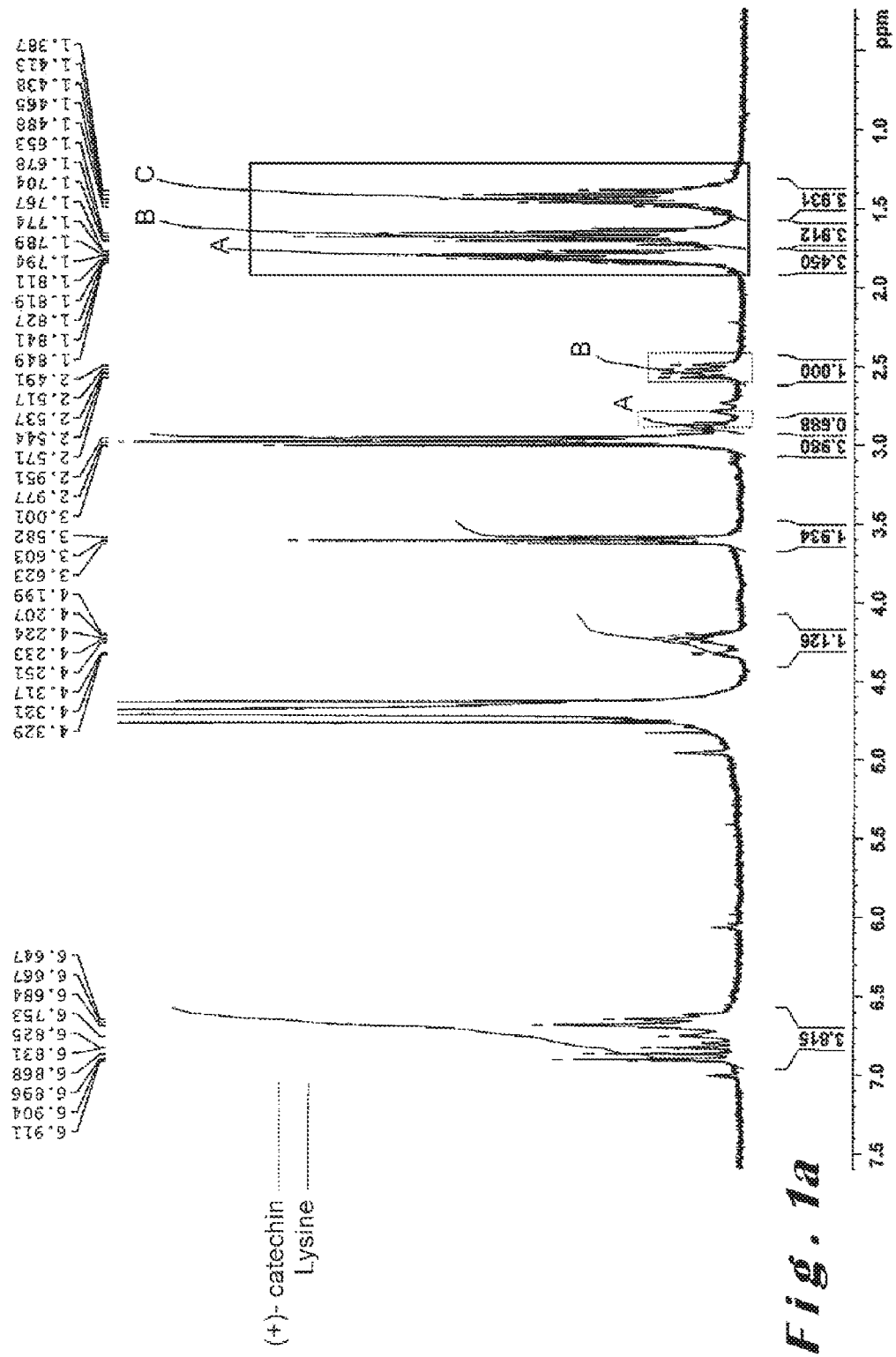
FIG. 1 illustrates the NMR spectra of the complex of monomeric (+)-catechin and of lysine for a molar equivalence ratio of 1:2 (a) and a molar equivalence ratio of 1:1 (b).

In the description, examples 1 to 6 and also comparative examples 1 to 5 relate to the results of bioavailability per os and of anticancer activity obtained in mammals (rats and human beings) for the composition based on the [C:AA/1:1-1:2.5] complex according to the invention.

Comparative examples 6 to 10 describe the results of bioavailability per os obtained in rats for the composition based on the mixture of monomeric (+)-catechin and of at least one basic amino acid or of at least one derivative of a basic amino acid in a molar equivalence ratio of between 1:1 and 1:2.5, preferably between 1:1 and 1:2.

In the context of the present invention, the equivalence between the results of the tests obtained in rats and in human beings has also been demonstrated. It is therefore proven that the results obtained in rats are actually reproduced in human beings.

In the examples which follow, with the exception of the results of table 7b, the contents of (+)-catechins in the blood correspond to the contents of monomeric free (+)-catechin.

Materials and Methods: Bioavailability Measurement

The bioavailability corresponds to the proportion of free monomeric (+)-catechin which is found in the organism compared with the amount initially administered.

In the context of the present invention, and in a nonlimiting manner, the (+)-catechin can be absorbed in the form of the [C:AA] complex or in the form of pure monomeric (+)-catechin, i.e. which is not linked to at least one basic amino acid or at least one basic amino acid derivative.

In the context of the present invention, it is first of all necessary to distinguish, the (+)-catechin having been absorbed, the presence in the blood of free monomeric (+)-catechin, i.e. in a non-conjugated form, from the conjugated (+)-catechin, i.e. which has been derivatized by the mammal's metabolism.

The derivatized monomeric (+)-catechin results from the cycle of elimination of the free monomeric (+)-catechin in the blood by the metabolism (for example, and in a non-limiting manner, by the enterohepatic cycle).

The elimination of active substances (or molecules) foreign to the organism results from the joint action of several processes. It comprises the metabolic capacity of various organs, first and foremost the liver, and excretion in all its forms, in particular renal (urine), but also hepatic (bile).

This elimination metabolism provides the derivation of the monomeric (+)-catechin by means of a well-known bioconversion cycle which involves two metabolic phases according to the enzymatic conversion processes. The phase-I reactions and the phase-II reactions are therefore distinguished:

the phase-I reactions comprise the oxidation reactions which are predominantly located in the hepatic microsomes; the reduction reactions which are much less frequent and have been less well examined; and the hydrolysis reactions which constitute a banal metabolic pathway, which occurs in the liver, in various tissues and even in the plasma; and then the derivatives resulting from the phase-I reactions are then conjugated. It is this conjugation which constitutes the phase-II reactions, including glucuronidation which involves the conjugation of these derivatives with glucuronic acid.

In this context, a given bioavailability corresponds to a given proportion (or content) of free monomeric (+)-catechin in the blood after administration per os of monomeric (+)-catechin.

Procedure:

The experimental results described below were obtained on the basis of a study carried out in healthy human beings and in healthy Wistar rats weighing approximately 250 grams.

With regard to the studies carried out on rats, the individuals were housed in groups of a maximum of 4 individuals in a cage with sawdust litter at an ambient temperature of between 20° C. and 25° C., with illumination for 12 h out of 24 h. An acclimation period was observed before beginning the experiments.

During the experimental study, the rats had access to a standard commercial feed and to water ad libitum. The rats were given nothing to eat through the night preceding the administration of the source of active product, it being understood that the active product is monomeric (+)-catechin (or other polyphenols: quercetin and EGCG).

The rats received an administration per os of a volume of 5 ml of a solution of active product.

With regard to taking the blood samples from the rats and from the human beings, the blood was collected in tubes internally coated with EDTA and was then centrifuged at 3000 rpm (revolutions per minute) at ambient temperature for 45 min, and then for 15 min at a temperature of 4° C. The plasma was then collected and stored at −70° C. before analysis.

The analytical technique (LC-MS/MS for Liquid Chromatography coupled to tandem Mass Spectrometry) for measuring the active substance in the blood was based on the method described by Mata-Bilbao et al., published in 2007 in the *Journal of Agricultural and Food Chemistry*, volume 55, page 8857.

With regard to the methodological development, the reference plasmas were collected internally, from rats and from cows not treated with the active substance, and then stored at −20° C.

The free (+)-catechin was extracted from the plasma with a solution of phosphoric acid, EDTA and ascorbic acid and was then purified by SPE (solid phase extraction); in particular, it is an Oasis™ HLB extraction which is analyzed by LC-MS/MS. The quantification was carried out according to a standard calibration procedure with (+/−)-catechin-2,3,4-$^{13}C_3$ as internal standard (SI).

In this context, the content of free (+)-catechin summarizes not only the content of monomeric free (+)-catechin isolated from the plasma, but also its isomeric forms which result from the isomerization of the monomeric free (+)-catechin pertaining to the conditions for extraction of the free (+)-catechin from said plasma.

The procedure is identical with regard to the extraction and the quantification of free quercetin or ECGC in the blood.

With regard to the extraction and quantification of the total (+)-catechin, the procedure is the same as that applied to the free (+)-catechin, with the exception of the fact that an additional step prior to the purification by SPE is carried out. This additional step consists in treating the sample with a digestive solution of arylsulfates and glucoronidase, in order to extract the active substance from the plasma cells.

The total concentration (ct) of (+)-catechin (free or derivatized) is calculated by measuring, for example using the trapezium method, the area under the curve of evolution of the plasma concentrations (cc) measured in ng/ml over time after oral administration of the source of monomeric (+)-catechin.

Standards

A solution of internal standard of 1 mg/ml (methanol) of (+)-catechin was prepared from stock (+)-catechin and was then stored at −20° C.

The catechin-C13 (reference: 719579, purity of 99.3% by weight) produced by Sigma Aldrich was used as SI.

The SI solution for the quantification of the (free and total) (+)-catechin was prepared by diluting 5 ml of the stock solution in methanol in a final volume of 10 ml. This SI solution was then stored at −20° C.

Methods a) Extraction Protocol for Analysis of the Free Monomeric (+)-Catechin in the Plasma transfer of 500 μl of homogenized plasma into a 15 ml flask;

addition of 50 μl of SI (10 ppm);

addition of 180 μl of an antioxidant solution (20 mg/ml of ascorbic acid and 1 mg/ml of EDTA) and 10 μl of ortho-phosphoric acid;

vortex mixing for 2 min;

addition of 1.5 ml of water for dilution in order to obtain an extraction mixture;

solid-phase extraction applied to the extraction mixture using Water Oasis™ HLB according to the standard protocol well known to those skilled in the art and adaptable to the present procedure;

drying of the eluent by evaporation at 45° C. under an inert atmosphere;

solubilization of the dry extract in acetonitrile, followed by centrifugation at 3000 rpm for 10 min; and HPLC (for high performance liquid chromatography) analysis.

b) Extraction Protocol for Analysis of the Total Monomeric (+)-Catechin in the Plasma transfer of 500 μl of homogenized plasma into a 15 ml flask;

addition of 50 μl of SI (10 ppm);

addition of 180 μl of an antioxidant solution (20 mg/ml of ascorbic acid in 1 mg/ml of EDTA) and 10 μl of ortho-phosphoric acid;

vortex mixing for 2 min;

addition of 750 μl of a 0.2 M acetate buffer solution (pH of 4.8);

addition of 5 μl of a mixture of *Helix pomatia* which follows a step of digestion of the solution for 2 hours at 55° C.;

centrifugation at 4000 rpm for 10 min in order to obtain an extraction mixture;

solid-phase extraction applied to the extraction mixture using Water Oasis™ HLB according to the standard protocol well known to those skilled in the art and adaptable to the present procedure;

drying of the eluent by evaporation at 45° C. under inert atmosphere;

solubilization of the dry extract in acetonitrile, followed by centrifugation at 3000 rpm for 10 min; and HPLC (for high performance liquid chromatography) analysis.

c) Extraction—Water Oasis™ HLB

Activation solution:

1 ml of methanol;

1 ml of water; and 1 ml of a solution of DMF (70% by volume) containing 0.1% (by volume) of formic acid.

Washing solution:
  E ml of water;
  1 ml of a methanol solution (30% by volume);
  1 ml of ethyl acetate.
Elution solution
  5 ml of a mixture of ethyl acetate and methanol in a molar equivalence ratio of 1:2.
d) LC-MS/MS Analysis
Liquid chromatography (LC)
column: Alltima C18 5μ;
HPLC aqueous mobile phase A: formic acid (concentrated in an amount of 0.1% by volume);
HPLC mobile phase B: solution of acetonitrile containing formic acid in an amount of 0.1% by volume;
flow rate: 0.6 ml/min;
oven temperature: 30° C.; and
injection volume: 50 μl;
elution program:

| Time (min) | A (% by volume) | B (% by volume) |
|---|---|---|
| 0.00 | 95 | 5 |
| 0.50 | 95 | 5 |
| 4.00 | 100 | 0 |
| 4.50 | 100 | 0 |
| 5.50 | 95 | 5 |
| 8.00 | 95 | 5 |

Mass Spectroscopy (MS)
negative-mode ESI ionization with a desolvation temperature of 400° C.;
source temperature: 120° C.;
cone gas flow: 150 l/h;
desolvation gas flow: 1000 l/h.

Synthesis of the Complex According to the Invention

The complex corresponds to a molecular structure in which the monomeric (+)-catechin is bonded to said at least one basic amino acid, or to said at least one basic amino acid derivative, by bonds of hydrogen bridge type.

This means that the complex does not dissociate in aqueous solution.

The monomeric (+)-catechin corresponds to a polyphenol present in the form of a monomer.

The basic amino acid has a radical which is positively charged at neutral pH.

The basic amino acid derivative, for its part, is defined in the context of the present invention as a molecule originating from a basic amino acid, and which results from one or more chemical conversions performed on this amino acid.

Preferentially, the complex (optionally in salt form) comprises monomeric (+)-catechin and at least one amino acid precursor which is a molecule intended to be converted into an amino acid or into an amino acid derivative after oral administration.

For example, and in a nonlimiting manner, the amino acid precursor may be a glucuronide or a glucuronoside of an amino acid, which, once absorbed, is converted by the organism into an amino acid, by virtue of the action of β-glucuronidase enzymes.

Example 1: Preparation of a Complex of Monomeric (+)-Catechin and of Lysine

1a. Complex of Monomeric (+)-Catechin and of Lysine in a Molar Equivalence Ratio of 1:2

Monomeric (+)-catechin, extracted from *Uncaria gambir* according to one of the methods well known to those skilled in the art, is milled and then dried at 50° C. under vacuum for 30 minutes.

After this drying step, the (+)-catechin extracted comprises water at least in trace amounts.

Two equivalents of lysine are then added successively to the (+)-catechin with stirring until dissolution in distilled water into which helium is bubbled. The solution is then heated up to a temperature between 40° C. and 45° C. and stirred for approximately one hour until complete dissolution of the two equivalents of lysine and is then placed in a fridge for 16 h.

Alternatively, the (+)-catechin can be added to a solution of two equivalents of lysine, brought to a temperature between 40° C. and 45° C. with stirring.

The solution is then filtered through a buchner funnel and washed with 50 ml of distilled water and then dried with evaporation of the water first in a rotary evaporator and then using a vacuum line (for 4 h at a temperature of 50° C.).

The product obtained is not soluble in deuterated methanol but is soluble in deuterated water ($D_2O$, solvent used for the NMR analysis). The NMR spectrum obtained is illustrated in FIG. 1a.

On reading the NMR spectrum, it is observed that the complex is made up of two mol of lysine for one mol of monomeric (+)-catechin.

Moreover, the presence of the three peaks A, B and C on the spectrum shows that the lysine is indeed bonded to the catechin. A strong modification of the aromatic peaks of the (+)-catechin, with disappearance of the peaks around 5.95-5.87 ppm and poor integration of the peaks at 6.50-7.00 ppm, is in fact observed. This indicates that there is an interaction between the lysine and the aromatic rings of the (+)-catechin, at the level of the phenolic groups, these interactions involving bonds of hydrogen bridge type.

X-ray diffraction spectra collected using a Siemens D5000 powder diffractometer with a Cu Kα radiation ($\lambda$=1.542 Å) were taken for the following compounds: the monomeric (+)-catechin (JE143), a mixture (JECatLysH) of lysine hydrochloride, of monomeric (+)-catechin and of protonated lysine (mixture C:Lys:HCl/1:2:2), and three mixtures of monomeric (+)-catechin and of non-protonated lysine (JE149b, JE150, JE151). The data were recorded in a range of between 5° and 60° in steps of 0.0167°.

Figure 4A:
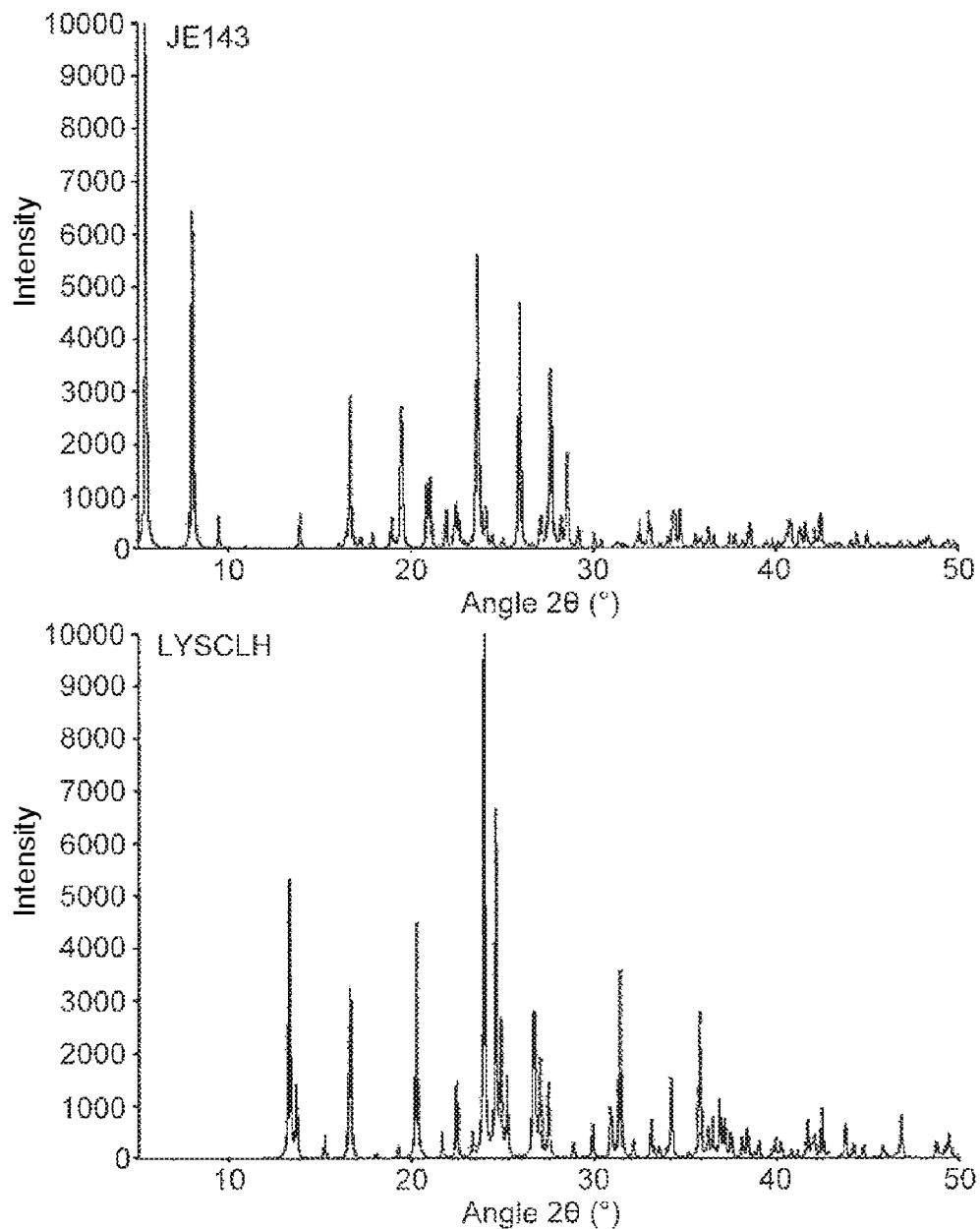
FIG. 4 illustrates the (powder) X-ray diffraction spectrum of the complex of monomeric (+)-catechin and of lysine for a molar equivalence ratio of 1:2.
Figure 4B:
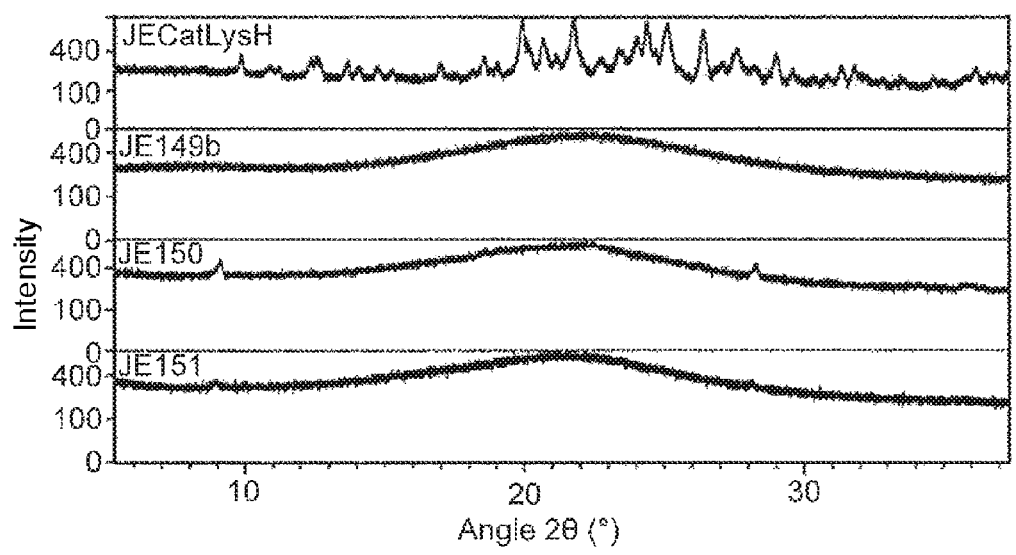

The spectra are illustrated in FIG. 4. As shown in FIG. 4a, associated with the JECatLysH sample is an XRD spectrum which does not appear to be an overlap of the spectra of the monomeric (+)-catechin and of the lysine hydrochloride, thus showing the formation of a complex and not a mixture of the two components. In particular, the disappearance of the peaks at the angles of 31.5 and 36 degrees of the lysine in the spectrum of the complex is, inter alia, noted.

The spectra for the three mixtures of monomeric (+)-catechin and of non-protonated lysine (JE149b, JE150, JE151) do not show any indication of crystallinity for these compounds, thereby indicating that, for these references JE149b, JE150 and JE151, there is formation of a composition in the amorphous crystalline state, contrary to what is observed for the JECatLysH mixture for which a crystalline network was identified, which does not correspond to the superposition of the spectra of the lysine hydrochloride and of the monomeric (+)-catechin.

1b. Complex of Monomeric (+)-Catechin and of Lysine in a Molar Equivalence Ratio of 1:1

The complex of monomeric (+)-catechin with lysine in a molar equivalence ratio of 1:1 was synthesized according to the same protocol as that used for the synthesis of the lysine complex of example 1a, but with the amount of lysine being reduced by a factor of 2 so that there is an excess of (+)-catechin which promotes the formation of said complex in a molar equivalence ratio of 1:1 by virtue of the lysine deficit.

Figure 1B:
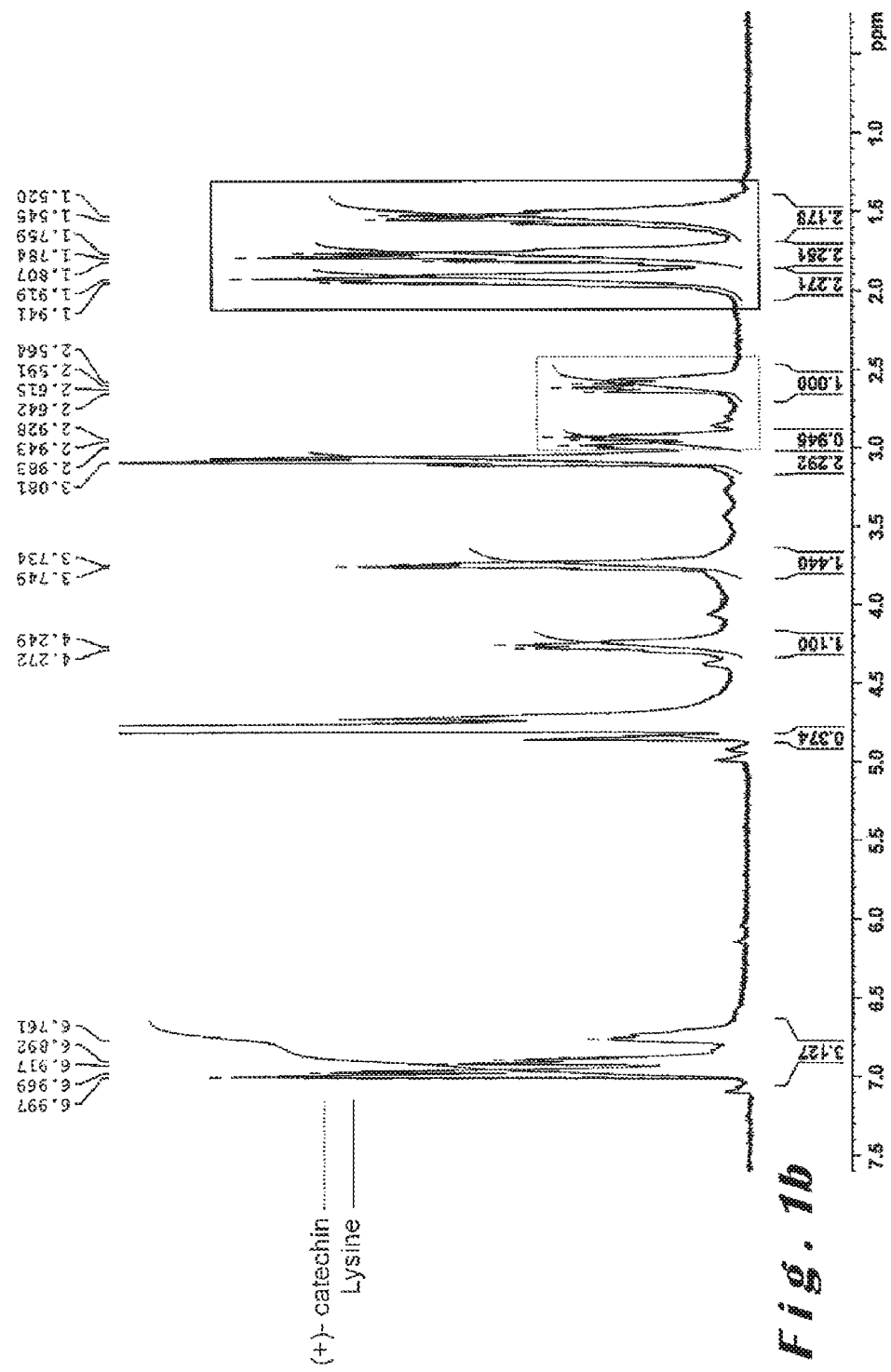

The NMR spectrum taken in deuterated water is illustrated in FIG. 1b. On reading the NMR spectrum, it is observed that the complex is made up of one mol of lysine for one mol of monomeric (+)-catechin.

Example 2: Preparation of a Complex of Monomeric (+)-Catechin and of Arginine 2a. Complex of Monomeric (+)-Catechin and of Arginine in a Molar Equivalence Ratio of 1:2

The complex of monomeric (+)-catechin with arginine was synthesized according to the same protocol as that used in the synthesis of the lysine complex of example 1a.

Figure 2A:
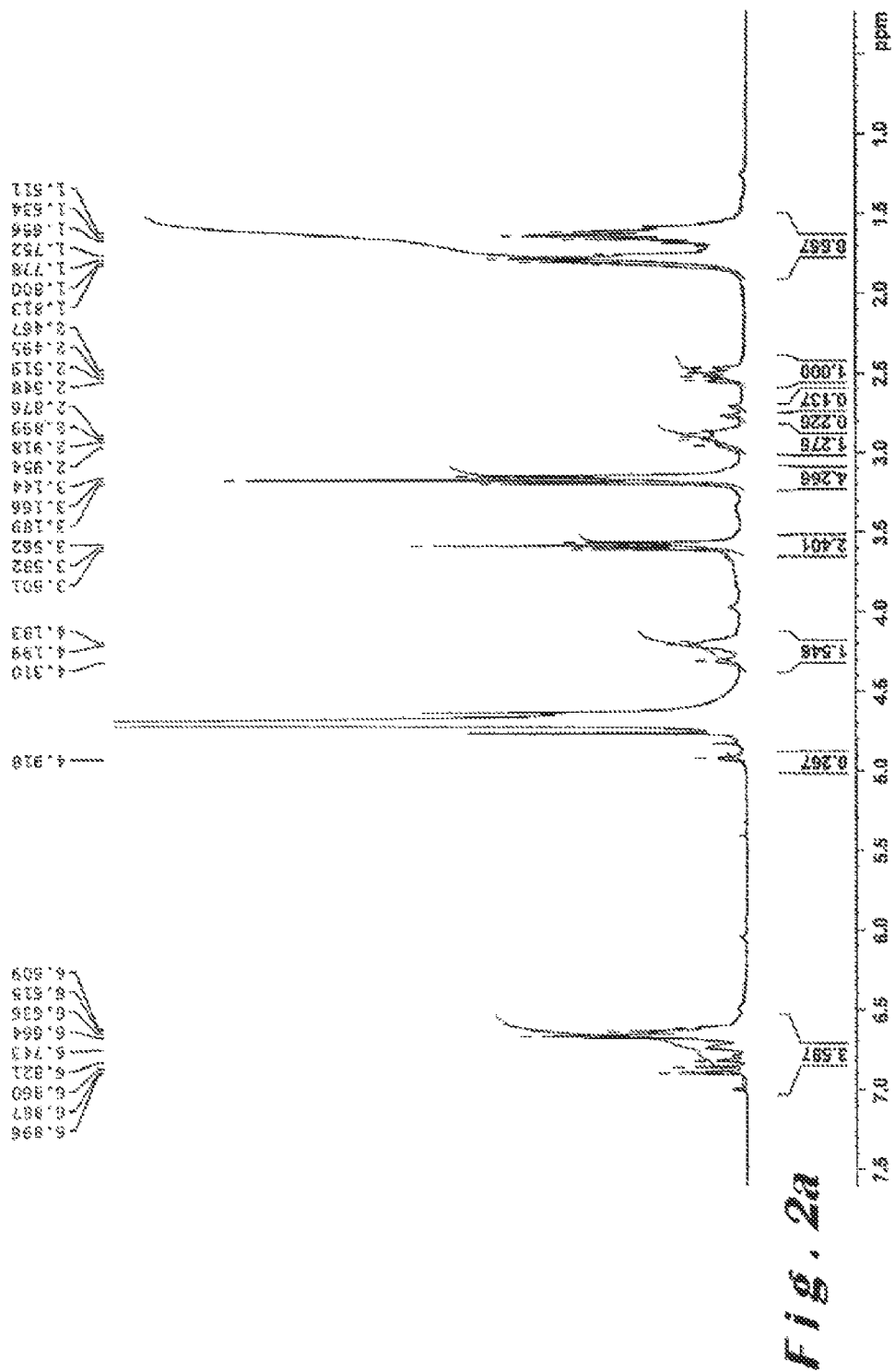
FIG. 2 illustrates the NMR spectra of the complex of monomeric (+)-catechin and of arginine for a molar equivalence ratio of 1:2 (a) and a molar equivalence ratio of 1:1 (b).

On reading the NMR spectrum illustrated in FIG. 2a, it is observed that the complex is made up of two molecules of arginine bonded, via bonds of hydrogen bridge type, to one molecule of monomeric (+)-catechin.

2b. Complex of Monomeric (+)-Catechin and of Arginine in a Molar Equivalence Ratio of 1:1

The complex of monomeric (+)-catechin with arginine was synthesized with the same protocol as that used in the synthesis of the lysine complex of example 1 b.

Figure 2B:
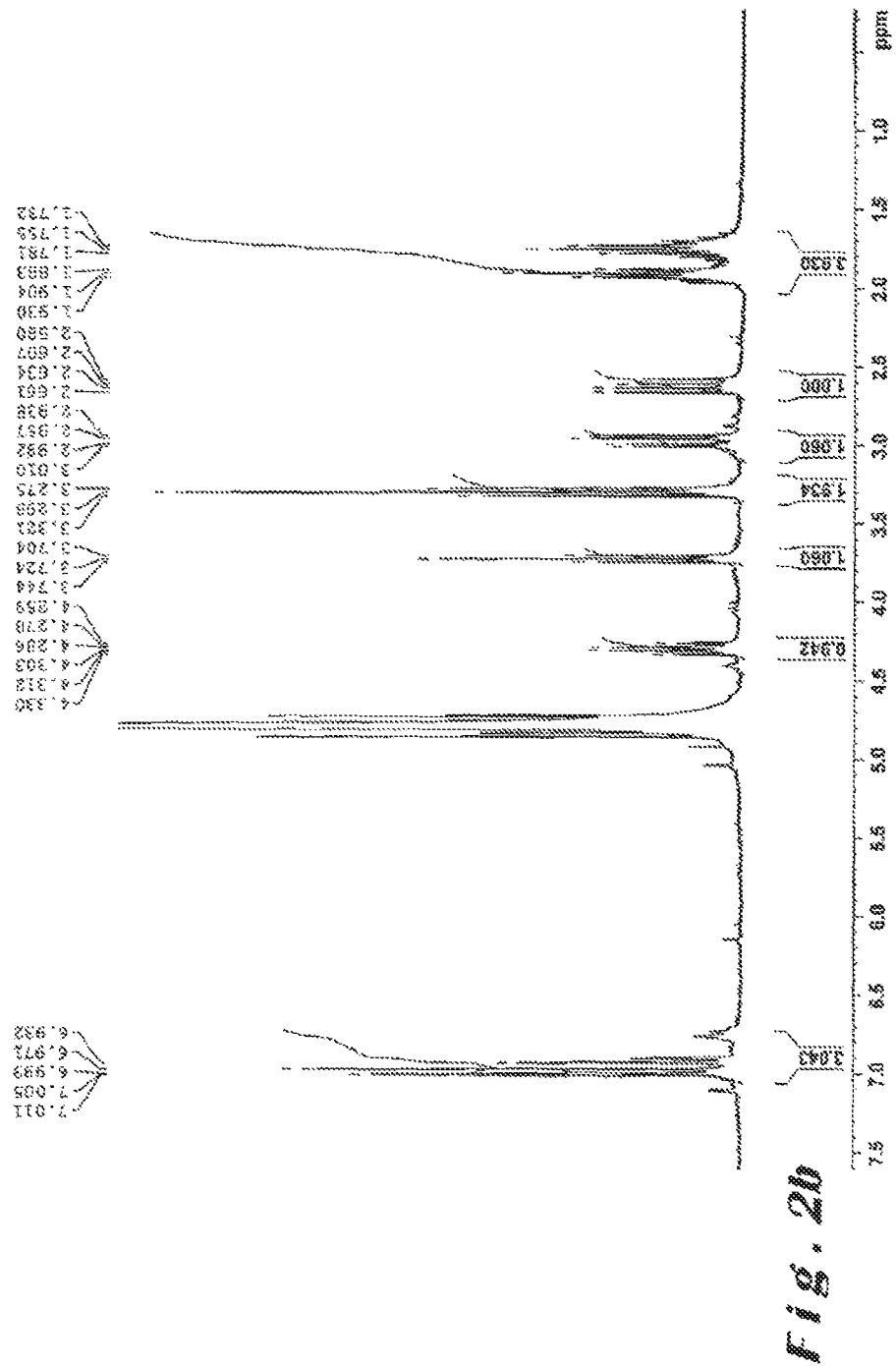

On reading the NMR spectrum of said complex illustrated in FIG. 2b, it is observed that the complex is made up of one molecule of arginine bonded, via bonds of hydrogen bridge type, to one molecule of monomeric (+)-catechin.

Bioavailability after Oral Administration of the Complex According to the Invention

Example 3: Measurement of the Bioavailability after Oral Administration of Monomeric (+)-Catechin Hydrochlorolysinate (or [C:Lys:HCl] Complex Salt) in Human Beings 1.5 g of a complex of monomeric (+)-catechin and of at least one basic amino acid: monomeric (+)-catechin hydrochlorolysinate is used. Starting from the [C:Lys] complex obtained according to protocol 1b, the monomeric (+)-catechin is present in a proportion of 61% by weight relative to the total weight of said complex (i.e. 0.92 g for 1.5 g), the monomeric (+)-catechin hydrochlorolysinate [C:Lys:HCl] complex salt) is synthesized by neutralization of said [C:Lys] complex with HCl added in an amount equimolar to that of said complex.

In this way, a complex salt is formed in which the lysine is bonded to the proton (Lys-H+) resulting from the HCl and in which the chloride (Cl-anion) is free in solution and does not interact with the [C:Lys-H+] complex.

This complex salt is administered to a group A of 5 healthy volunteers.

The content of free monomeric (+)-catechin in the blood was measured for the group A of volunteers, over time, after 1.5 g of monomeric (+)-catechin hydrochlorolysinate containing 0.92 g of monomeric (+)-catechin had been taken (table 1).

TABLE 1 plasma concentration (cc) of free monomeric (+)-catechin (in ng/ml) for the group A as a function of time T (hours)

| T (h) | Group A cc (ng/ml) |
|---|---|
| 0.5 | 524 ± 30 |
| 1 | 487 ± 47 |
| 2 | 328 ± 35 |
| 3 | 173 ± 38 |
| 4 | 78 ± 24 |
| 6 | 16 ± 2 |

TABLE 2 parameters for evaluating the bioavailability after oral administration, calculated from the curves of plasma concentrations (cc) of the free monomeric (+)-catechin (in ng/ml) for the group A as a function of time T (hours)

| | Group A |
|---|---|
| T (max) (h) | 0.5 |
| ct (ng h/ml) (ng min/ml) | 1263 ± 88 (75780) |
| c (max) (ng/ml) | 525 |

Figure 3:
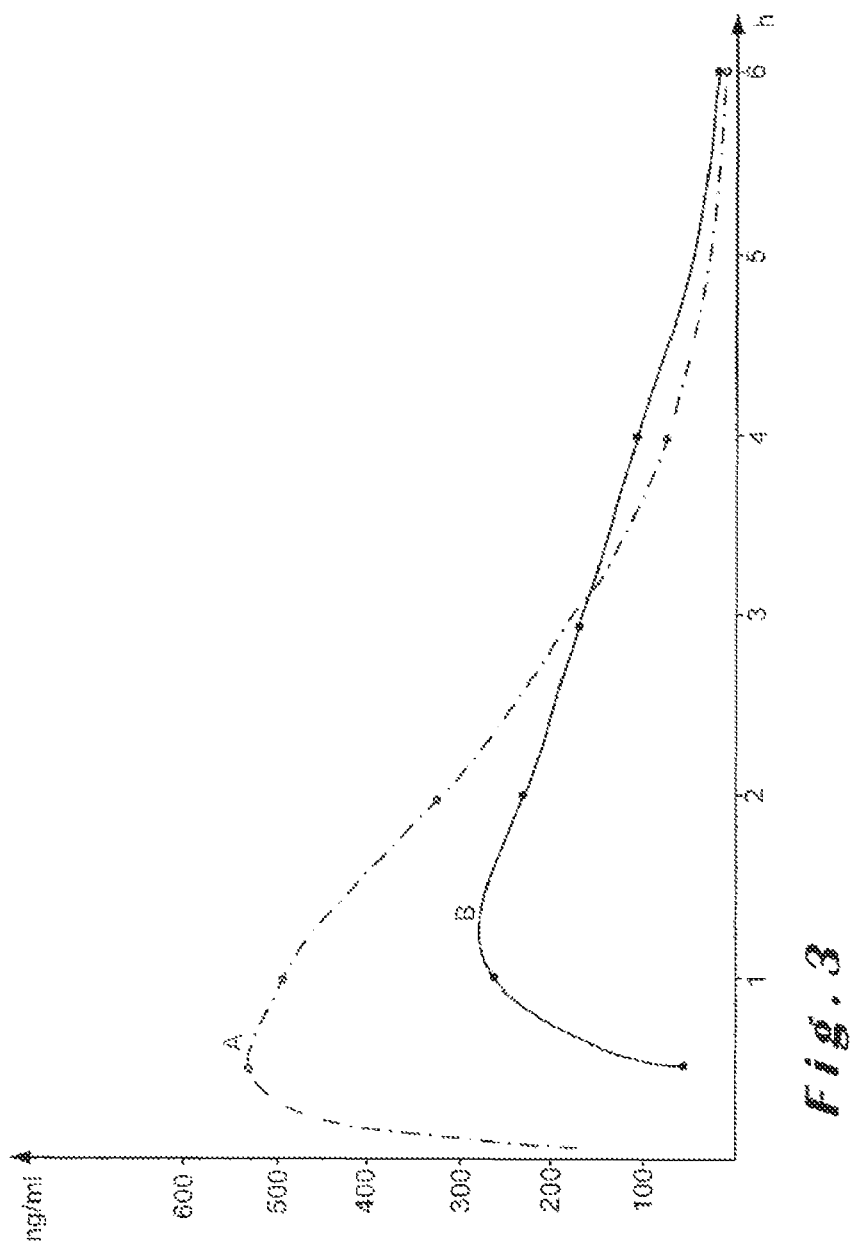
FIG. 3 illustrates the evolution of the plasma concentrations (cc) of free (+)-catechin measured in human beings in ng/ml over time T (hours) after the assimilation of (+)-catechin hydrochlorolysine (rich in monomeric (+)-catechin in an amount of 61% by weight, group A) and of one gram of pure monomeric (+)-catechin (group B).

FIG. 3 illustrates the evolution of the plasma concentrations (cc) measured in ng/ml over time T (hours) after oral administration of (+)-catechin hydrochlorolysinate (curve A); this curve is extrapolated from the data listed in table 1.

The area measured, for example using the trapezium method well known in the literature, under the curve indicates the total concentration (ct) of free monomeric (+)-catechin assimilated in the plasma, measured over a period of six hours starting from the ingestion of the (+)-catechin in the form of a complex formed with the hydrochlorolysinate. This ct parameter makes it possible to calculate, from the data of table 1, the bioavailability of the (+)-catechin expressed in ng h/ml. The ct is 1263±88 ng h/ml for the (+)-catechin hydrochlorolysinate.

From FIG. 3, the maximum concentration c (max) corresponds to the peak of the curve. For the group having received the [C:Lys:HCl] complex salt, the c (max) reaches 525 ng/ml. This maximum concentration is reached at a time T (max) of 0.5 h for the group A having received the monomeric (+)-catechin complex.

Comparative Example 1: Measurement of the Bioavailability after Oral Administration of Pure Monomeric (+)-Catechin in Human Beings A dose of 1 g of pure monomeric (+)-catechin is administered to a group B of 5 healthy volunteers.

The content of free monomeric (+)-catechin in the blood was measured for the group of volunteers B over time after (+)-catechin had been taken. The results are indicated in table 3.

TABLE 3 plasma concentration (cc) of free monomeric (+)-catechin (in ng/ml) for the group B as a function of time T (hours)

| T (h) | Group B cc (ng/ml) |
|---|---|
| 0.5 | 59 ± 61 |
| 1 | 266 ± 147 |

TABLE 3-continued plasma concentration (cc) of free
monomeric (+)-catechin (in ng/ml)
for the group B as a function
of time T (hours)

| T (h) | Group B cc (ng/ml) |
|---|---|
| 2 | 230 ± 87 |
| 3 | 226 ± 38 |
| 4 | 128 ± 51 |
| 6 | 27 ± 13 |

TABLE 4 parameters for evaluating the bioavailability after oral
administration, calculated from the curves of plasma
concentrations (cc) of the free monomeric (+)-catechin (in
ng/ml) for the group B as a function of time T (hours)

| | Group B |
|---|---|
| T (max) (h) | 1.20 |
| ct (ng h/ml) (ng min/ml) | 904 ± 163 (54240) |
| c (max) (ng/ml) | 280 |

FIG. 3 illustrates the evolution of the plasma concentrations (cc) measured in ng/ml over time T (hours) after oral administration of pure (+)-catechin (curve B). This curve is extrapolated from the data listed in table 3.

The area measured under the curve indicates the total concentration (ct) of free monomeric (+)-catechin assimilated in the plasma, measured over a period of six hours starting from the ingestion of the pure (+)-catechin. This ct parameter makes it possible to calculate, from the data of tables 1 and 3, the bioavailability of the (+)-catechin, expressed in ng h/ml. The ct is calculated at 1263±88 ng h/ml for 1.5 g of (+)-catechin hydrochlorolysinate containing 0.92 g of pure (+)-catechin. It is calculated at 904±163 ng h/ml for 1 g of pure (+)-catechin, i.e. at 832±150 ng h/ml for 0.92 g of pure (+)-catechin, corresponding to the dose ingested with the [C:Lys:HCl] complex salt (see example 2 according to the invention), that is to say an improvement in bioavailability of at least 52%.

In FIG. 3, the maximum concentrations c (max) correspond to the peaks of the curves. For the group having received 1 g of pure monomeric (+)-catechin, the c (max) is calculated at 280 ng/ml, i.e. 258 ng/ml for 0.92 g of pure (+)-catechin corresponding to the dose of (+)-catechin ingested with the [C:Lys:HCl] complex salt. For the group having received the [C:Lys:HCl] complex salt, the c (max) reaches 525 ng/ml, which corresponds to an increase of 103% compared with the pure (+)-catechin. These maximum concentrations are reached respectively at a time T (max) of 1.20 h for the group B and of 0.5 h for the group having been treated with the monomeric (+)-catechin complex.

From this first comparative example, it is shown that the (+)-catechin complex, and in particular the (+)-catechin hydrochlorolysinate, significantly improved (+52%) the bioavailability after oral administration of the monomeric (+)-catechin compared with the taking thereof in pure form. The speed with which the monomeric (+)-catechin passes into the blood (and is then in free form in the plasma), measured by the T (max) parameter, and also the maximum concentration, c (max), are also very significantly increased: respectively by +166% and by +103%, compared with taking monomeric (+)-catechin in its pure form.

Comparative Example 2: Measurement of the
Bioavailability after Oral Administration of the
Pure Monomeric (+)-Catechin and of the Complex
of (+)-Catechin and of Lysine in Rats A dose of 100 mg (per kg of body weight) of pure monomeric (+)-catechin (CP) or a dose of (+)-catechin lysinate equivalent to 100 mg of (+)-catechin was administered to each individual of a sample of 5 Wistar rats.

The parameters for evaluating the bioavailability after oral administration are given in table 5 for various sources of (+)-catechin: CP, or various lysine complexes.

TABLE 5 parameters for evaluating the bioavailability after oral
administration, calculated from the curves of plasma concentrations
(cc) of free monomeric (+)-catechin (in ng/ml) for each source of
(+)-catechin, as a function of time T (minutes)

| | Source of monomeric (+)-catechin | | | |
|---|---|---|---|---|
| | CP | [C:Lys/ 1:1] | [C:Lys:HCL/ 1:1:1] | [C:Lys/ 1:2] |
| T (max) (min) | 60 | 60 | 60 | 120 |
| c (max) (ng/ml) | 716 | 1127 | 955 | 1547 |
| ct (ng min/ml) | 96 238 | 112 422 | 132 349 | 186 348 |
| Δct (as %) | 0 | +17 | +36 | +94 |

In this table, the Δct (expressed as %) corresponds to the measurement of the difference between the ct obtained with each of the complexes and the ct measured for the pure monomeric (+)-catechin, related back to the bioavailability value for the CP. By way of illustration, the Δct calculated for the [C:Lys/1:1] complex is obtained as follows:

100×[(112 422−96 238)/96 238]=17%

The best parameter values are achieved for the [C:Lys/1:2] complex for which a value of bioavailability after oral administration of close to $1.9 \times 10^5$ ng min/ml is achieved, which corresponds to an increase of 94% compared with the (+)-catechin ingested in pure form.

Furthermore, the maximum concentration [C(max)] of catechin having passed into the blood is increased by 116%; the peak which gives this Cmax is located at 120 min [T (max)] compared with 60 min for the other sources, which also has the effect of favorably increasing the blood levels of free monomeric (+)-catechin over time, confirming the delayed action of the active substance and therefore an improved anticancer action.

These data correspond to what we had found in human beings by comparing the oral intake of pure (+)-catechin (table 4) to that of the [C:Lys:HCL, 1:1:1] complex salt (table 2). The bioavailabilities are in fact increased in the same proportions, +52% in humans, +36% in rats.

In the present example, in rats, we show that the [C:Lys/1:2] complex increases even more significantly the bioavailability of the (+)-catechin after oral administration.

Comparative Example 3: Measurement of the
Bioavailability after Oral Administration of the
Pure Monomeric (+)-Catechin, of the Complex of
(+)-Catechin and of Arginine, and of the Complex
of (+)-Catechin and of Lysine, in Rats A dose of 100 mg (per kg of body weight) of pure monomeric (+)-catechin (CP) or a dose of (+)-catechin complex equivalent to 100 mg of (+)-catechin was administered to each individual of a sample of 5 Wistar rats.

The parameters for evaluating the bioavailability after oral administration are given in table 6 for various sources of (+)-catechin: CP, or various lysine complexes or arginine complexes.

TABLE 6 parameters for evaluating the bioavailability after oral administration, calculated from the curves of plasma concentrations (cc) of free monomeric (+)-catechin (in ng/ml) for each source of (+)-catechin, as a function of time T (minutes)

| | Source of monomeric (+)-catechin | | |
|---|---|---|---|
| | CP | [C:Lys/1:1] | [C:Arg/1:1] |
| T (max) (min) | 60 | 60 | 60 |
| c (max) (ng/ml) | 716 | 1127 | 1292 |
| ct (ng min/ml) | 96 238 | 112 422 | 116 351 |
| Δct (as %) | 0 | +17 | +21 |

From these results, it is deduced that any basic amino acid (i.e. chosen from lysine, arginine and histidine) which bonds to the (+)-catechin, and therefore which neutralizes the acidity of the ortho-diphenol groups located on the nucleus of the (+)-catechin, could have the same beneficial effect on the bioavailability of said catechin after oral administration.

Comparative Example 4: Measurement of the Bioavailability after Oral Administration of the Pure Monomeric (+)-Catechin, and of the Complex of (+)-Catechin and of Lysine, at a Molar Equivalence Ratio of 1:1 and 1:5, in Rats A dose of 25 mg (per kg of body weight) of pure monomeric (+)-catechin (CP) or a dose of (+)-catechin lysinate equivalent to 25 mg of (+)-catechin was administered to each individual of a sample of 3 Wistar rats.

The parameters for evaluating the bioavailability after oral administration are given in table 7a for various sources of (+)-catechin: CP, or various lysine complexes.

The T (max), c (max) and ct parameters in terms of total (+)-catechin present in the blood are given in table 7b. The total (+)-catechin summarizes the free monomeric (+)-catechin and the monomeric (+)-catechin which has been conjugated by the rat's body.

TABLE 7a parameters for evaluating the bioavailability after oral administration, calculated from the curves of plasma concentrations (cc) of free monomeric (+)-catechin (in ng/ml) for each source of (+)-catechin as a function of time T (minutes)

| | Source of monomeric (+)-catechin | | |
|---|---|---|---|
| | CP | [C:Lys/1:2] | [C:Lys/1:5] |
| T (max) (min) | 30 | 60 | 60 |
| c (max) (ng/ml) | 154 | 173 | 74 |
| ct (ng min/ml) | 21 145 | 24 845 | 13 770 |
| Δct (as %) | 0 | +17 | −35 |

TABLE 7b

T (max), c (max) and ct parameters in terms of total (+)-catechin present in the blood, calculated from the curves of plasma concentrations (cc) of total monomeric (+)-catechin (in ng/ml) for each source of (+)-catechin as a function of time T (minutes)

| | Source of monomeric (+)-catechin | | |
|---|---|---|---|
| | CP | [C:Lys/1:2] | [C:Lys/1:5] |
| T (max) (min) | 30 | 60 | 60 |
| c (max) (ng/ml) | 2200 | 2366 | 1100 |
| ct (ng min/ml) | 273 875 | 339 245 | 163 080 |
| Δct (as %) | 0 | +24 | −40 |

The [C:Lys/1:2] complex allows an increase in the contents of both free and total plasma (+)-catechin, while the [C:Lys/1:5] complex clearly decreases these contents compared with the pure (+)-catechin, i.e. the (+)-catechin ingested without lysine.

The results of this example, compared to the results illustrated in table 5, show that the optimum in terms of bioavailability after oral administration is actually achieved for the [C:AA/1:2] complex, optionally in the presence of HCl. It should be noted that the presence of an acid favorably influences the parameters of bioavailability after oral administration (see table 5); however, the presence of this acid is not essential to obtain an increased bioavailability after oral administration.

Anticancer Action of the Complex According to the Invention

Example 4: Measurement of the Action of Monomeric (+)-Catechin Hydrochlorolysinate and of Monomeric (+)-Catechin Ascorbolysinate on the Total Incorporation and Incorporation into Collagen of 3H-Proline in the Skin The stabilization of lysosome membranes prevents the release of the proteolytic enzymes responsible for the degradation of the connective matrix, in particular of collagen. This degradation is responsible for the propagation of metastatic cancer cells, whatever the type of cancer (*Cell Communication and Signaling* 2010, 8: 22).

The skin is a tissue particularly rich in connective matrix and in collagen fibers, which gives it all its elasticity.

The effectiveness of the (+)-catechin hydrochlorolysinate and of the monomeric (+)-catechin ascorbolysinate, administered orally, on the one hand on the total incorporation (on the entire skin) and on the other hand the incorporation into the collagen of said skin, of 3H-proline is demonstrated here.

To do this, a study was carried out in vivo on a batch of 24 female Wistar rats weighing from 95 to 115 g, divided into two groups C and D, each of 12 rats. For each group, the radioactive 3H-hydroxyproline, the specific activity of which is 13.6 Ci/10-3 mol, was administered to all the animals by intraperitoneal injection of 3H-proline at a dose, relative to the weight of the individuals, of 1 mCi/kg, which represents an activity in terms of radioactive 3H-proline of 100 μCi/individual.

6 rats of each group received a treatment based on monomeric (+)-catechin by gavage in a proportion of 100 mg/kg for 5 days before sacrifice. The other 6 rats which did not receive treatment based on monomeric (+)-catechin are a control subgroup (ctrl). The group C received monomeric (+)-catechin hydrochlorolysinate, while the group D received monomeric (+)-catechin ascorbolysinate.

TABLE 8 action of the monomeric (+)-catechin in its complex forms (100 mg/kg) on the level (in dpm/mg) of total incorporation (IT) and incorporation into collagen (IC) of 3H-hydroxyproline in rat skin

| Level | Group C ctrl | C treated | D ctrl | D treated |
|---|---|---|---|---|
| IT | 5620 ± 186 | 6248 ± 124 | 4864 ± 231 | 5112 ± 259 |
| IC | 1178 ± 39 | 1343 ± 48 | 963 ± 42 | 1117 ± 49 |

In table 8, the level of incorporation is measured by the number of disintegrations of the radioactive 3H-hydroxyproline per minute (dpm) per mg of dry weight. The higher this number, the higher the concentration of 3H-hydroxyproline.

The results of table 8 show that the catechin and the complex of (+)-catechin hydrochlorolysinate stimulate connective tissue biosynthesis and particularly collagen synthesis.

In addition, this example, according to the invention, confirms the protection of the connective web in vivo by oral absorption of the monomeric (+)-catechin complexes given orally and, consequently, the protection of this web, in particular against the intrusion of cancer cells.

Comparative Example 5: Measurement of the Action of the Pure Monomeric (+)-Catechin on the Total Incorporation and the Incorporation into Collagen of 3H-Proline in the Skin In this comparative example, a group E of 12 Wistar rats weighing from 95 to 115 g, in which radioactive 3H-hydroxyproline, the specific activity of which is 13.6 Ci/10-3 mol, was administered to all the individuals by intraperitoneal injection of 3H-proline at a dose, relative to the weight of the individuals, of 1 mCi/kg, which represents an activity in terms of radioactive 3H-proline of 100 µCi/individual.

6 rats of each group received a treatment based on pure monomeric (+)-catechin by gavage in a proportion of 100 mg/kg for 5 days before sacrifice. The other 6 rats which did not receive treatment based on monomeric (+)-catechin are a control subgroup (ctrl).

TABLE 9 action of the pure monomeric (+)-catechin (100 mg/kg) on the level (in dpm/mg) of total incorporation (IT) and incorporation into collagen (IC) of 3H-hydroxyproline in rat skin

| Level | Group E ctrl | Group E treated |
|---|---|---|
| IT | 4864 ± 231 | 5689 ± 410 |
| IC | 963 ± 42 | 1124 ± 51 |

In table 9, the level of incorporation is measured by the number of disintegrations of the radioactive 3H-hydroxyproline per minute (dpm) per mg of dry weight. The higher this number, the higher the concentration of 3H-hydroxyproline.

The results of tables 8 and 9 show that the increase in the level of incorporation for the complexes of monomeric (+)-catechin hydrochlorolysinate (+15%) and of monomeric (+)-catechin ascorbolysinate (+14%) is equivalent to that measured when the rats are given pure monomeric (+)-catechin by gavage (+16%).

This comparative example confirms the protection of the connective web in vivo by oral absorption of the monomeric (+)-catechin complexes given orally and, consequently, the protection of this web in particular against cancer cell intrusion, this being at monomeric (+)-catechin contents which are de facto lower (61 mg of (+)-catechin for 100 mg of complex) than that encountered when pure (+)-catechin is taken (100 mg of (+)-catechin).

Example 5: Measurement of the Action of the Monomeric (+)-Catechin Hydrochlorolysinate ([C:Lys:HCl] Complex Salt) on the Incidence of Gastric Ulcers and on the Histamine Level in the Gastric Mucosa in Mastomys Rats In this example, the effectiveness of the monomeric (+)-catechin hydrochlorolysinate in vivo in an African rat, Mastomys, which is known to spontaneously generate gastric lesions and in particular gastric carcinomas, is demonstrated.

Mastomys in fact has a special system of cells which store histamine in the gastric mucosa; these cells can give rise to carcinoid tumors.

In this example, a sample of n=48 Mastomys are sensitized a first time by intraperitoneal injection of 3 µg of ovalbumin dissolved in 0.2 ml of saline solution containing 1 mg of aluminum hydroxide which brings about anti-immunoglobulin E (IgE) and G (IgG) antibodies. After 7 days, a second injection of 1 mg of ovalbumin in 0.01 ml of saline solution is given in the gastric mucosa at the level of the corpus of the anesthetized animals, which causes an ulcerated lesion at the actual site of the injection.

The 48 rats are divided up into three groups: one of 24 and two of 12 individuals. The first group of 24 individuals (G1) received a placebo (concentrated NaCl solution at 0.15 M).

The second group (G2) of 12 individuals was treated with the monomeric (+)-catechin hydrochlorolysinate administered per os twice a day (2×300 mg), two days before the injection and three days after injection. The third group (G3) of 12 individuals received, under the same conditions as those of the G2 group, the monomeric (+)-catechin hydrochlorolysinate in a proportion of 100 mg, but intraperitoneally.

As shown by the results of table 10, the oral administration of the (+)-catechin hydrochlorolysinate gives a very significant decrease (−72%) in the number of animals exhibiting a gastric ulcer (NU) and also a significant decrease (−18%) in the histamine level (HL), this level being expressed as $10^{-6}$ mg/kg of protein, in the gastric mucosa. The histamine level is measured for the G1, G2 and G3 groups on the basis of a sample of n=12 individuals.

The decrease in the level of histamine accumulated in the gastric mucosa results directly from the action of the monomeric (+)-catechin on the wall of the cells which store histamine. By contributing to the reinforcement of the wall of these cells, the monomeric (+)-catechin makes it possible to decrease the level of histamine assimilated in the gastric mucosa and therefore to reduce the number of ulcers.

It is interesting to note, with respect to this experiment, that in particular in many types of chronic or acute leukemias, an increase in mast cells is found, with a concomitant increase in histamine levels and also an increase in immunoglobulin levels (*Blood Cells Mol. Dis.* 35 (3), 370-383, 2005).

TABLE 10 action of the (+)-catechin hydrochlorolysinate on the incidence of gastric ulcers and on the histamine level in the gastric mucosa in *Mastomys*

| Group | n | NU | HL (n = 12) |
|---|---|---|---|
| G1 | 24 | 23 | 46.17 ± 2.30 |
| G2 | 12 | 5 | 37.91 ± 3.73 |
| G3 | 12 | 6 | 34.98 ± 3.52 |

Example 6: Measurement of the Action of the Monomeric (+)-Catechin Hydrochlorolysinate ([C:Lys:HCl] Complex Salt) in the Treatment of Patients Suffering from Cancer In this example, the results relating to the test of the effect of the monomeric (+)-catechin hydrochlorolysinate in two cancer patients treated for more than a year with a tablet of 500 mg of [C:Lys:HCl] complex salt per day are presented.

In the first patient, a 67-year-old man, a lymphoplasmocytic lymphoma (of Waldenström macroglobulinemia type) was detected during a post-operative blood test on day Do. The diagnosis is based on the electrophoretic detection of a monoclonal peak of immunoglobulins (IgM). This diagnosis was reconfirmed and the peak was assayed during a second analysis using the same detection by electrophoresis.

Immunoglobulins play an essential role in the organism's defense against attacks and are normally secreted by B lymphocytes.

In multiple myeloma or, for example, in the case of Waldenström's disease, secretion of a single type of immunoglobulin, or monoclonal immunoglobulin, by plasma cells present in the bone marrow and which proliferate in an uncontrolled manner, is observed.

These immunoglobulins are found at a high concentration in the blood and in the urine. They therefore constitute real tumor markers. The assaying thereof gives an account of the number of sick cells and the extent of the disease and, consequently, makes it possible to monitor its progression under treatment.

Successive blood tests gave the following data for the IgM assay (in mg per 100 ml of plasma):

TABLE 11 evolution of the IgM level (in mg/100 ml) in the blood over time

| Sampling period | IgM |
|---|---|
| $D_0$ | 1910 |
| $D_0$ + 1 month | 2010 |
| $D_0$ + 5 months | 1966 |
| $D_0$ + 8 months | 2467 |
| $D_0$ + 12 months | 2280 |
| $D_0$ + 15 months | 2748 |
| $D_T$ | 2931 |
| $D_T$ + 4 months | 2417 |
| $D_T$ + 9 months | 2410 |
| $D_T$ + 15 months | 2412 |

The results of table 11 show that, since the taking of monomeric (+)-catechin hydrochlorolysinate for a year and a half, there has been a stabilization below the maximum detected on day $D_T$ starting from which the treatment was administered.

The level of infiltration remained low, despite IgM values greater than 2000 mg/100 ml. In addition, the patient did not undergo chemotherapy treatment. It is therefore considered that he is stabilized.

In the second patient, a left subclavicular cervical adenopathy was first of all detected on day Do. Next, 2 weeks later, a left renal adenocarcinoma was detected for this patient, which was followed by a nephrectomy of the left kidney 3 days after the detection of the adenocarcinoma in this kidney.

Thereafter, on day $D_0$+3 months, a left cervical lymph node dissection is performed on the patient. This procedure was followed by a series of 15 radiotherapy sessions.

Starting from day $D_0$+15 months (that is to say on day $D_T$), the patient was orally administered a tablet of 500 mg of (+)-catechin hydrochlorolysinate per day.

On day $D_T$+15 months, the appearance of a pathological mediastinal adenopathy (45 cm$^3$ in volume) was observed and required a mediastinal lymph node dissection followed by a pulmonary examination on day $D_T$+17 months. This examination demonstrated the involution of a small micronodular opacity of 5 mm in the left lung and the absence of secondary lesion at the level of the pulmonary parenchyma and of the abdominal stage.

On $D_T$+19 months, the consultation report concluded that the clear cell renal carcinoma was in complete remission. This diagnosis was reconfirmed during controlled examinations carried out on $D_T$+23 months. Clearly, it appears that taking (+)-catechin hydrochlorolysinate for one year stabilized the patient's condition.

Synthesis of the Composition of Precursors of the Complex or of the Complex Salt According to the Invention The method for producing the composition comprising said monomeric (+)-catechin and said at least one basic amino acid as precursor of said complex comprises the following steps:

providing a first amount of monomeric (+)-catechin;

providing a second amount of at least one basic amino acid, or of at least one basic amino acid derivative, so as to obtain a molar equivalence ratio between said (+)-catechin and said at least one basic amino acid or said at least one basic amino acid derivative of between 1:1 and 1:2.5, preferably greater than or equal to 1:1, in particular greater than 1:1, preferably less than or equal to 1:2.5, in particular less than 2.5, more particularly less than or equal to 1:2, more particularly less than 2; and bringing said monomeric (+)-catechin into contact with said at least one basic amino acid, or with said basic amino acid derivative, so as to obtain said mixture of monomeric (+)-catechin and of at least one basic amino acid or of at least one derivative of a basic amino acid.

Preferentially, the method comprises an additional step which consists in providing an acid, preferably an ascorbic acid.

Alternatively, the method comprises an additional step which consists in providing an aqueous phase and in solubilizing said mixture in said aqueous phase so as to form a complex of (+)-catechin and of at least one basic amino acid, said complex being solubilized in said aqueous phase.

Alternatively, the method also comprises a step of adding a biocompatibility excipient to said mixture according to the invention.

Preferably, said at least one amino acid provided is selected from the group consisting of lysine and arginine, of natural or synthetic origin, and of a mixture thereof.

In comparative examples 6 to 9 which follow, the orally administered composition was prepared based on a mixture of hydrochlorolysinate (Lys:HCl) in pulverulent form with pure monomeric (+)-catechin at the molar equivalent ratios of 1:1, 1:2, 1:3 and 1:5.

A composition which comprises the monomeric (+)-catechin and at least one basic amino acid as precursor of said [C:Lys:HCl] complex salt is obtained.

Each of the mixtures is then solubilized in water. During the solubilization of the mixture, formation of the complex of (+)-catechin and of hydrochlorolysinate in the aqueous phase occurs. The solution thus obtained is a solution of (+)-catechin hydrochlorolysinate in the form of a complex: the complex obtained in this solution is a complex of monomeric (+)-catechin and of at least one basic amino acid (or derivative thereof) with a molar equivalence ratio identical to that of the mixture according to the invention. Thus, a mixture of monomeric (+)-catechin and of an amino acid in a molar equivalence ratio of 1:1 will give, once solubilized in the aqueous phase, a solution of complex of monomeric (+)-catechin and of at least one basic amino acid (or derivative thereof) in a molar equivalence ratio equal to 1:1.

This solution is then administered per os (PO) or by intravenous (IV) injection to each individual of a group of 5 Wistar rats, at a dose of 25 mg (per kilogram of body weight) of pure monomeric (+)-catechin or a dose of (+)-catechin lysinate equivalent to 25 mg of (+)-catechin.

Bioavailability after Oral Administration of the Composition of Precursors of the Complex or of the Complex Salt According to the Invention Comparative Example 6: Measurement of the Bioavailability after Oral Administration and after Administration by Injection of the Complex of (+)-Catechin and of Lysine, at a Molar Equivalence Ratio of 1:1 and 1:2, in Rats TABLE 12a plasma concentration (cc) of the total monomeric (+)-catechin (in ng/ml) as a function of time T (min)

| | IV | | PO |
|---|---|---|---|
| | [C:Lys:HCl/ 1:2:2] | [C:Lys:HCl/ 1:1:1] | [C:Lys:HCl/ 1:2:2] |
| T (min) | | cc (ng/ml) | |
| 10 | 8066 | 6406 | 1839 |
| 30 | 2639 | 2259 | 3780 |
| 60 | 1191 | 963 | 3190 |
| 120 | 338 | 270 | 1990 |
| 240 | 0 | 0 | 475 |

TABLE 12b plasma concentration (cc) of the free monomeric (+)-catechin (in ng/ml) as a function of time T (min)

| | IV [C:Lys:HCl/ 1:2:2] | PO [C:Lys:HCl/ 1:2:2] |
|---|---|---|
| T (min) | | cc (ng/ml) |
| 10 | 3340 | 428 |
| 30 | 991 | 1027 |
| 60 | 291 | 1188 |
| 120 | 0 | 767 |
| 240 | 0 | 179 |

TABLE 12c comparison of the total plasma concentrations (ct) in ng min/ml of the free monomeric (+)-catechin and of the total monomeric (+)-catechin after intravenous and oral administration of 25 mg/kg of C:Lys:HCl/1:2:2 in rats

| | IV | PO |
|---|---|---|
| Free | 87 970 | 165 325 (Δct*: +88%) |
| Total | 277 040 | 479 585 (Δct*: +73%) |

*Δct measured between the IV and PO data.

After intravenous injection of the [C:Lys:HCl/1:2:2] complex salt, the plasma levels (cc) of (+)-catechin, naturally very high at the start, very rapidly come back down to very low levels, 340 ng/ml after 2 hours for the total (+)-catechin found in the plasma and 0 ng/ml for the free (+)-catechin, whereas the total blood levels of the same product taken orally under the same conditions are maintained after 2 hours at 1990 ng/ml and the amount of free (+)-catechin at 767 ng/ml, as indicated in the results summarized in tables 12a and 12b.

This intravenous injection (made possible thanks to the hydrochlorolysinate making the (+)-catechin soluble) shows, whether there is or are one or two molecules of lysine linked to the monomeric (+)-catechin, that this (+)-catechin is rapidly eliminated from the blood stream.

On the other hand, the oral ingestion of the complexed form of the monomeric (+)-catechin, on the one hand, increases the amounts of free monomeric (+)-catechin in the blood and, on the other hand, prolongs the maximum concentration peak.

This is a surprising result. Indeed, the plasma levels obtained after direct injection into the blood give blood levels that are much higher over the first hour after administration than when the product is given orally, which is expected. On the other hand, when the complex is administered per os, free monomeric (+)-catechin ct values which are increased by 88% with regard to the free (+)-catechin available in the plasma are observed (ct of 165 325 ng min/ml for an administration per os compared with only 87 970 ng min/ml for an IV administration); the same is true for the total catechin found in the plasma; the ct increases in the same manner by 73%, which is absolutely remarkable. Oral administration therefore surprisingly proves to be superior to intravenous administration for the overall bioavailability, whether it is free or total, of the (+)-catechin in the plasma after administration of the [C:Lys:HCl/1:2:2] complex salt.

Furthermore, while, after 120 min, there is virtually no more (+)-catechin in the blood after IV injection, the maximum levels of catechin in the blood are observed, at the same moment, after oral intake of the [C:Lys:HCl/1:2:2] complex salt.

It is therefore demonstrated that the [C:Lys:HCl/1:2:2] complex salt improves the bioavailability of the catechin in a surprising manner; indeed, this blood bioavailability of the (+)-catechin, whether it is free or conjugated, is surprisingly better when administered orally than when administered by intravenous injection.

This shows that the levels and the bioavailability data after intravenous administration cannot be extrapolated to oral administration and that the results of the present invention clearly differ from document U.S. Pat. No. 4,285,964 in which no bioavailability test for an intake per os was exemplified.

Comparative Example 7: Measurement of the Effect of the Acid on the Bioavailability after Oral Administration of the Complex of (+)-Catechin and of Lysine in Rats In order to verify the possible effect of the addition of an acid to the [C:Lys/1:2] complex, we measured the levels of free monomeric (+)-catechin in the plasma after oral ingestion of CP or of the [C:Lys:HCl/1:2:2] complex salt. The results are given in the table below:

TABLE 13

T (max), c (max) and ct parameters in terms of free (+)-catechin present in the blood, calculated from the curves of plasma concentrations (cc) of the free monomeric (+)-catechin (in ng/ml) for each source of (+)-catechin as a function of time T (minutes)

|  | Source of monomeric (+)-catechin | |
| --- | --- | --- |
|  | CP | [C:Lys:HCl/1:2:2] |
| T (max) (min) | 60 | 60 |
| c (max) (ng/ml) | 580 | 1200 |
| ct (ng min/ml) | 91 935 | 165 325 |
| Δct (as %) | 0 | +77 |

The positive effect of the 2 molecules of lysine on the bioavailability of the monomeric (+)-catechin and on its maximum concentration is again found; the addition of 2 molecules of HCl influences the effect of the 2 molecules of lysine: Δct of +77% in the presence of HCl and of +17% without HCl (see table 7a).

Figure 5:
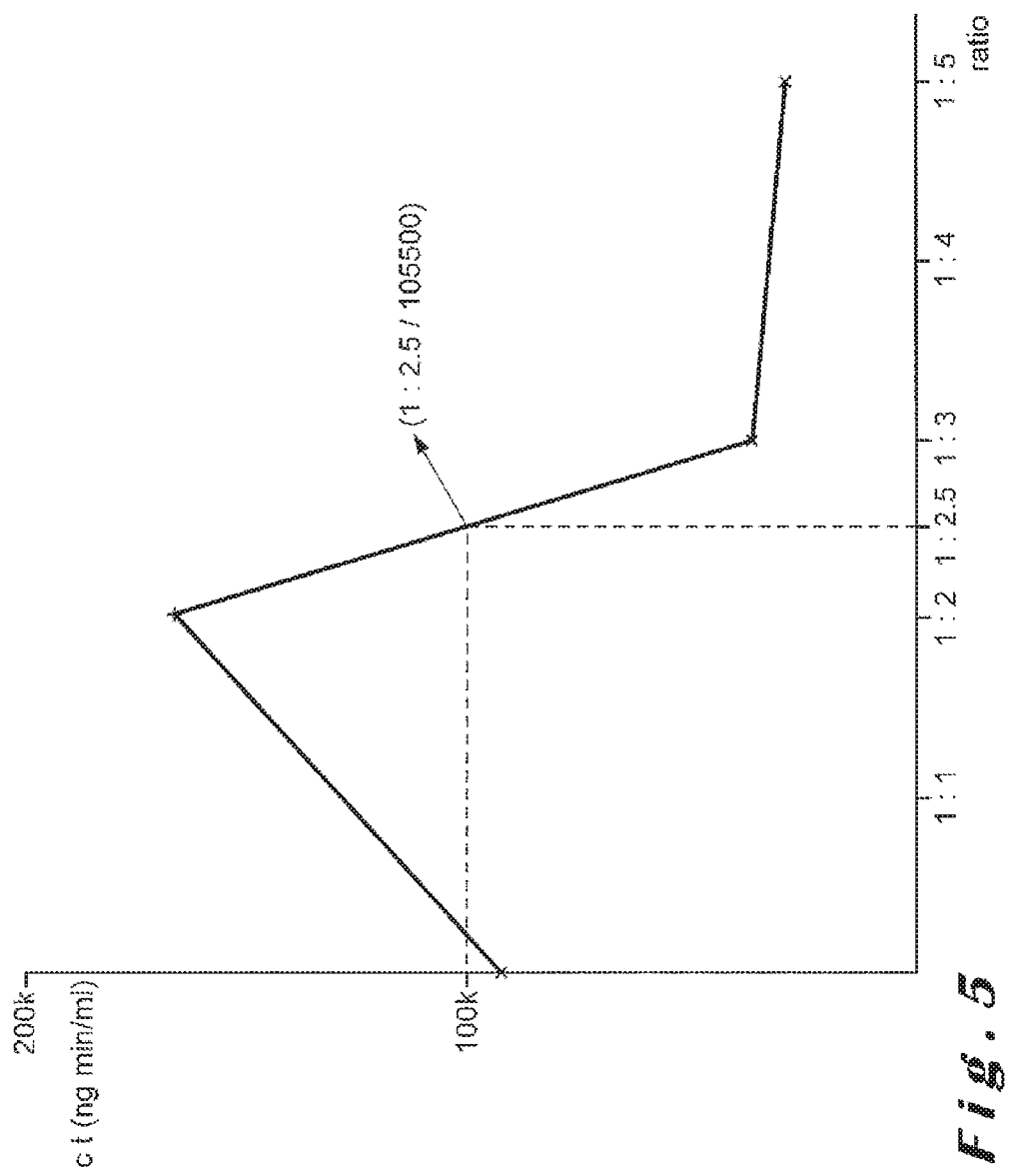
FIG. 5 illustrates the evolution of the concentration of free monomeric (+)-catechin in the plasma as a function of the molar equivalence ratio between the monomeric (+)-catechin and the lysine: 1:0, 1:1, 1:2, 1:2.5, 1:3, and 1:5, for a [C:Lys:HCl] complex salt (see table 14).

Comparative Example 8: Measurement, in Rats, of the Effect of the Molar Equivalence Ratio Between the (+)-Catechin and the Basic Amino Acid on the Bioavailability after Oral Administration of the Complex of (+)-Catechin Hydrochlorolysinate According to the Invention The value of the ct (ng min/ml) for the C:Lys:HCl/1:1.5:1.5 complex salt reported on the curve in FIG. 5 is 142 k ng min/ml, that is to say better than for 1:1:1 (127 k, reported value) and better than for 1:2.5:2.5 (105 k ng min/ml, reported value), but not as good as for 1:2:2 (165 k, calculated value).

All the ct values obtained for (+)-catechin salts in proportions less than or equal to 1:2.5:2.5 are much better than the values obtained for these same salts in higher proportions, 1:3:3 (38 k, calculated value) and 1:5:5 (26 k, calculated value).

These results confirm the results of comparative example 4: the [C:Lys:HCl/1:2:2] complex salt is the only (+)-catechin-lysine association which clearly improves the bioavailability of the (+)-catechin taken orally.

The data of this example not only show that the [C:Lys:HCl/1:2:2] complex salt gives an optimum bioavailability, but also that, as soon as this proportion is exceeded, the effect is clearly reversed, with a Δct of −59% for the molar equivalence ratio of 1:3:3 and of −66% for the molar equivalence ratio of 1:5:5.

In addition, the separate ingestion (within a time period of between 5 and 10 min) of the monomeric (+)-catechin and the hydrochlorolysinate gives a negative effect (with a Δct of −48%) on the amount of free monomeric (+)-catechin in the plasma. This demonstrates that the catechin and the lysine must be mixed before ingestion (in a form solubilized optionally in water), or at least ingested simultaneously.

Comparative Example 9: Measurement, in Rats, of the Nature of the Therapeutic Composition on the Bioavailability after Oral Administration Whether the composition administered per os is based on the [C:AA/1:1-1:2.5] complex prepared according to the method described in example 1a (1b) or 2a (2b) (see examples 1 and 2), or else the composition administered per os is a mixture in a desired molar equivalence ratio of a powder of (+)-catechin and of lysine hydrochloride (also referred to as hydrochlorolysinate), the results in terms of bioavailabilities after oral administration are similar (see table 15 below).

TABLE 14

T (max), c (max) and ct parameters in terms of free (+)-catechin present in the blood, calculated from the curves of plasma concentrations (cc) of the free monomeric (+)-catechin (in ng/ml) for each source of (+)-catechin as a function of time T (minutes)

|  | Source of monomeric (+)-catechin | | | | | |
| --- | --- | --- | --- | --- | --- | --- |
|  |  | Ratio | | | | |
|  | CP | 1:2:2 | 1:2.5:2.5 | 1:3:3 | 1:5:5 | 1:2:2[§] |
| T (max) (min) | 60 | 60 | — | 60 | 60 | 60 |
| c (max) (ng/ml) | 580 | 1200 | — | 280 | 265 | 226 |
| ct (ng min/ml) | 91 935 | 165 325 | 105 500* | 38 000 | 31 136 | 44 095 |
| Δct (as %) | 0 | +80 | +15 | −59 | −66 | −48 |

*ct value estimated from the profile of the curve of evolution of ct as a function of the monomeric (+)-catechin:lysine molar equivalence ratio (see FIG. 5). The other ct values estimated at the start in FIG. 5 are those of the 1:1.5:1.5 ratio, which is 142 000 ng min/ml, and of the 1:1:1 ratio, which is 127 000 ng min/ml.
[§]Separate per os intake of the hydrochlorolysinate and of the pure (+)-catechin.

Given the results of comparative example 2 in which the [C:Lys/1:2] complex was prepared according to protocol 1a (see example 1), and the results of comparative example 8, in which the [C:Lys:HCl/1:2:2] complex salt was prepared by simply mixing one mol of pulverulent (+)-catechin and two mol of pulverulent hydrochlorolysinate and then dissolving before administration per os, the results summarized in table 15 show that the improvement in bioavailability after oral administration for these complexes remains in the same order of magnitude.

TABLE 15

T (max), c (max) and ct parameters in terms of free (+)-catechin present in the blood, calculated from the curves of plasma concentrations (cc) of the free monomeric (+)-catechin (in ng/ml) for each source of (+)-catechin as a function of time T (minutes)

| | Source of monomeric (+)-catechin | |
|---|---|---|
| | [C:Lys/1:2] | [C:Lys:HCl/1:2:2] |
| T (max) (min) | 120 | 60 |
| c (max) (ng/ml) | 1547 | 1200 |
| ct (ng min/ml) | 186 348 | 165 325 |
| Δct (as %) | +94 | +80 |

Being able to obtain optimum bioavailability parameters on the basis of a pulverulent mixture of (+)-catechin and of amino acid represents an advantage in terms of production cost as long as the preparation of this mixture is carried out in a single solid phase and very easily, thereby making it possible to envision large-scale production perspectives.

Comparative Example 10: Measurement, in Rats, of the Bioavailability after Oral Administration for Quercetin and Epigallocatechin Gallate (EGCG)

In this example, it is demonstrated that the effect of lysine is not significant, either on the bioavailability after oral administration of quercetin, or on that of epigllocatechin gallate (EGCG), as shown by the results of table 16 below:

TABLE 16

T (max), c (max) and ct parameters in terms of free polyphenol present in the blood, calculated from the curves of plasma concentrations (cc) of the polyphenol (in nq/ml) for each polyphenol source as a function of time T (minutes)

| | Source of monomeric (+)-catechin | |
|---|---|---|
| | QP | [Q:Lys:HCl/1:2:2]§ |
| T (max) (min) | 60 | 60 |
| c (max) (ng/ml) | 10430 | 8777 |
| ct (ng min/ml) | 1 311 645 | 1 541 945 |
| Δct$^q$ (as %)** | 0 | +18 |

* QP: pure quercetin, i.e. not complexed with at least one basic amino acid;
§[Q:Lys:HCl/1:2:2]: complex of quercetin with two lysines.
**Δct$^q$: measurement of the difference between the ct obtained with the complex and the ct measured for the QP, related back to the bioavailability value for QP.

In this example, the orally administered composition was prepared based on a mixture of hydrochlorolysinate (Lys:HCl) in pulverulent form with pure monomeric quercetin or EGCG at the molar equivalence ratios of 1:2 for quercetin, and of 1:1, 1:2, 1:3 and 1:5 with regard to EGCG.

Each of the mixtures is solubilized in water. This solution is then administered per os (PO) to each individual of a group of 5 Wistar rats, in a proportion of one dose of 25 mg (per kg of body weight) of pure monomeric quercetin or EGCG or a dose of quercetin lysinate or EGCGC lysinate equivalent to 25 mg of polyphenol.

With regard to EGCG, the levels measured remain below the reliable limits of detection (i.e. below 250 ng/ml) whether for pure EGCG or for its complexed forms, whatever the proportion of hydrochlorolysinate added to the epigallocatechin gallate (in a molar equivalence ratio of 1:1:1, of 1:2:2, of 1:3:3, or else of 1:5:5).

In conclusion, in view of the results of optimum bioavailability obtained for a complex between the (+)-catechin and the basic amino acid at a molar equivalence ratio of 1:2, and given the fact that the attempts at complexation of other acid polyphenols such as quercetin or EGCG failed, it is clearly demonstrated in the context of the present invention that the [C:AA/1:1-1:2.5] complexes are complexes which have a specific activity with regard to its passage through the gastrointestinal tract. Clearly, it is not therefore a case of a simple acid-based neutralization, which should, in the latter case, have also promoted the bioavailability after oral administration of quercetin and of EGCG.

It is also understood that the present invention is in no way limited to the abovementioned particular embodiments and that many modifications may be introduced therein without departing from the context of the appended claims.

The invention claimed is:

1. A method for treating or reducing the risk of cancer in a patient, said method comprising administering to said patient a composition in an amount effective to treat or reduce the risk of cancer in a patient, the composition comprising a compound of monomeric (+)-catechin and at least one basic amino acid or at least one basic amino acid derivative, wherein said monomeric (+)-catechin has a molar equivalence ratio relative to said one basic amino acid or to said one basic amino acid derivative of between 1:1 and 1:2.5, wherein said at least one basic amino acid is selected from lysine, arginine or a mixture of lysine and arginine, wherein said at least one basic amino acid derivative is selected from the group consisting of a derivative of lysine, a derivative of arginine, and a mixture of a derivative of lysine and a derivative of arginine, and wherein the composition does not comprise an amino acid other than said lysine, arginine, or lysine or arginine derivative, or a mixture of said lysine and arginine or lysine and arginine derivatives.

2. The method according to claim 1, wherein said monomeric (+)-catechin has a molar equivalence ratio relative to said at least one basic amino acid or to one basic amino acid derivative of between 1:1.5 and 1:2.5.

3. The method according to claim 1, wherein said at least one basic amino acid is of natural or synthetic origin, or a mixture of the two.

4. The method according to claim 1, wherein said at least one basic amino acid is lysine.

5. The method according to claim 1, wherein said composition comprises at least one acid.

6. The method according to claim 5, wherein said acid is selected from the group consisting of ascorbic acid, acetic acid, citric acid and hydrochloric acid.

7. The method according to claim 5, wherein said acid is ascorbic acid.

8. The method according to claim 1, wherein said composition also comprises one or more biocompatible excipients.

9. The method according to claim 1, wherein the content of (+)-catechin and of basic amino acid or of derivative of a basic amino acid in said composition is between 15% and 95% by weight relative to the total weight of said composition, preferably between 60% and 90%, advantageously from 65% to 85%.

10. The method according to claim 1, wherein said composition is formulated for oral administration.

11. The method according to claim 1, wherein said composition is in liquid form.

12. The method according to claim 1, wherein said composition has a pH greater than or equal to 3 for a 0.01 molar solution at 25° C.

13. The method according to claim 1, wherein said composition is in solid form.

14. The method according to claim 1, wherein said composition is in the form of a powder, a tablet or a lozenge.

15. The method according to claim 1, wherein said monomeric (+)-catechin and said at least one basic amino acid or said at least one basic amino acid derivative form a complex.

16. The method according to claim 15, wherein said composition is in the form of a salt of said complex and further comprises at least one acid, said salt comprising said complex of said monomeric (+)-catechin and said at least one basic amino acid or said at least one basic amino acid derivative and at least one proton derived from at least one acid and at least one anion derived from said at least one acid, said salt exhibiting said proton and said anion in equimolar amount relative to the amount of basic amino acid or basic amino acid derivative.

17. The method according to claim 15, wherein said complex forms post-administration, said composition being a solid composition comprising said monomeric (+)-catechin and said at least one basic amino acid or said at least one basic amino acid derivative, and optionally an acid.

18. The method according to claim 1, wherein said composition is in solid form and comprises monomeric (+)-catechin and said at least one basic amino acid or said at least one basic amino acid derivative, and optionally an acid, wherein said composition is a precursor of a complex of said monomeric (+)-catechin and said at least one basic amino acid or said at least one basic amino acid derivative or of a salt of the complex, wherein said salt comprises said complex of said monomeric (+)-catechin and said at least one basic amino acid or said at least one basic amino acid derivative and at least one proton derived from the acid and at least one anion derived from the acid, said complex or said salt of said complex forming pre-oral administration as soon as said composition is placed in an aqueous solution, said monomeric (+)-catechin and said one basic amino acid or said one basic amino acid derivative being present in the composition in a molar equivalent ratio of between 1:1 and 1:2.5.

19. The method according to claim 1, wherein said cancer is selected from hepatocellular cancer, leukemia, myelomas and lymphoma.

20. The method according to claim 1, wherein said cancer is selected from liver cancer, prostate cancer, breast cancer, uterine cancer, testicular cancer, bladder cancer, kidney cancer, lung cancer, bronchial cancer, bone cancer, mouth cancer, esophageal cancer, stomach cancer, pancreatic cancer and colorectal cancer.

* * * * *